US009727040B2

(12) United States Patent
Luisi et al.

(10) Patent No.: US 9,727,040 B2
(45) Date of Patent: Aug. 8, 2017

(54) METHOD AND APPARATUS FOR AUTOMATICALLY GENERATING TRIM LINES FOR CRANIAL REMODELING DEVICES

(71) Applicant: CRANIAL TECHNOLOGIES, INC., Tempe, AZ (US)

(72) Inventors: Jerold N Luisi, Phoenix, AZ (US); Timothy R Littlefield, Phoenix, AZ (US); George E Kechter, Peoria, IL (US); Jeanne K Hertz, Scottsdale, AZ (US)

(73) Assignee: CRANIAL TECHNOLOGIES, INC., Tempe, AZ (US)

( * ) Notice: Subject to any disclaimer, the term of this patent is extended or adjusted under 35 U.S.C. 154(b) by 404 days.

(21) Appl. No.: 14/036,248

(22) Filed: Sep. 25, 2013

(65) Prior Publication Data
US 2014/0081440 A1 Mar. 20, 2014

Related U.S. Application Data

(60) Division of application No. 13/136,088, filed on Jul. 23, 2011, now Pat. No. 8,867,804, and a continuation-in-part of application No. 12/927,132, filed on Nov. 8, 2010, now Pat. No. 8,442,288.

(51) Int. Cl.
*G05B 19/042* (2006.01)
*A61F 5/058* (2006.01)
*G06F 17/50* (2006.01)

(52) U.S. Cl.
CPC ........ *G05B 19/042* (2013.01); *A61F 5/05891* (2013.01); *G06F 17/50* (2013.01); *Y10T 29/49* (2015.01)

(58) Field of Classification Search
None
See application file for complete search history.

(56) References Cited

U.S. PATENT DOCUMENTS

| | | | | |
|---|---|---|---|---|
| 5,094,229 A | * | 3/1992 | Pomatto | A61F 5/01 128/857 |
| 5,331,550 A | * | 7/1994 | Stafford | G06F 19/345 128/925 |
| 6,340,353 B1 | * | 1/2002 | Pomatto | A61F 5/05891 602/17 |

(Continued)

*Primary Examiner* — Tsung-Yin Tsai
(74) *Attorney, Agent, or Firm* — Donald J Lenkszus

(57) ABSTRACT

A method for manufacturing a custom cranial remodeling device of a type comprising plastic material is provided. The method includes the steps of: providing a first database of three-dimensional digital surface images of trim lines for cranial remodeling devices of a first type; providing a second database of three-dimensional digital surface images of trim lines for cranial remodeling devices of a second type; providing a first program for creating trim lines for a cranial remodeling device of the first type, the first program utilizing the first database; providing a second program for creating trim lines for a cranial remodeling device of the second type, the second program utilizing the second database; generating a three-dimensional model of a desired head shape; forming the plastic material onto the model; and selecting one of the first or the second programs to generate trim lines for the cranial remodeling device.

12 Claims, 21 Drawing Sheets

(56) References Cited

U.S. PATENT DOCUMENTS

| | | | |
|---|---|---|---|
| 6,423,019 B1* | 7/2002 | Papay | A61F 5/05891 602/17 |
| 6,529,758 B2* | 3/2003 | Shahidi | A61B 5/06 600/407 |
| 6,611,617 B1* | 8/2003 | Crampton | G01B 11/2518 356/614 |
| 8,114,039 B2* | 2/2012 | Qu | A42B 3/28 128/857 |
| 2002/0048396 A1* | 4/2002 | Bewley, Jr. | B44B 1/006 382/154 |
| 2004/0197016 A1* | 10/2004 | Littlefield | G01N 29/225 382/128 |
| 2004/0228519 A1* | 11/2004 | Littlefield | A61F 5/05891 382/154 |
| 2004/0230149 A1* | 11/2004 | Littlefield | G06T 1/0007 602/17 |
| 2004/0236708 A1* | 11/2004 | Littlefield | G06T 1/0007 706/16 |
| 2006/0094951 A1* | 5/2006 | Dean | A61F 2/30942 600/407 |
| 2012/0110828 A1* | 5/2012 | Luisi | A61F 5/05891 29/592 |

* cited by examiner

METHOD AND APPARATUS FOR AUTOMATICALLY GENERATING TRIM LINES FOR CRANIAL REMODELING DEVICES

FIELD OF THE INVENTION

This invention pertains to a method and system for automatically generating trim lines for cranial remodeling devices.

BACKGROUND OF THE INVENTION

Cranial remodeling is utilized to correct for deformities in the head shapes of infants. Prior to the development of the Dynamic Orthotic Cranioplasty$^{SM}$ method of cranial remodeling by Cranial Technologies, Inc, the assignee of the present invention, the only viable approach for correction of cranial deformities was surgical correction of the shape of the cranium. Dynamic Orthotic Cranioplasty$^{SM}$ utilizes a treatment protocol in which the DOC BAND® cranial remodeling device is custom produced for each subject to be treated.

In the past, custom cranial remodeling devices were produced by first obtaining a full size and accurate cast of the actual head shape of each subject. This cast was then modified to produce a second or desired head shape model. The second or desired head shape model is used to form the cranial remodeling band for the infant. In the past, the second or desired shaped head shape model was obtained by manually modifying the first cast to form the desired shape model.

Plastic materials are formed on the desired head shape model. Cut lines referred to as trim lines are marked by a highly skilled orthotist onto the plastic materials and then cuts in the plastic materials are made along the trim lines as a near final step in producing the cranial remodeling band Cranial Technologies has maintained a "library" of the casts of the head casts of infant's deformed heads and the corresponding models of the desired corrected head shapes.

Cranial Technologies, Inc. continued its pioneering developments with its proprietary DSI® digital image capturing system and its Digital Surface Imaging® methodology for the time efficient and safe image capture of three-dimensional full head images.

More specifically, the DSI® digital image capturing system was utilized to capture DSI® digital data representative of digital images of each cast of a deformed head and each corresponding model of the corrected head shape and store the DSI® digital data for each digital image in first and second databases, respectively. The first and second databases were utilized to train a neural network.

Cranial Technologies developed a system that utilized these first and second databases to automatically produces digital data representative of a modified head shape from DSI® digital data representative of a deformed head. A processor operable with a neural network program trains the neural network program with the first plurality of first sets of captured data stored in the first database and the second plurality of second sets of captured data stored in the second database such that the neural network is trained to operate on a new set of captured data for a first head shape to produce a corresponding modified head shape. In that system, a support vector machine program is operated to train the neural network program.

In the Cranial Technologies system, captured data for a deformed head is processed utilizing Principal Component Analysis (PCA) to generate PCA data representative of the deformed head. The PCA data is provided as input to the neural network. The neural network processes the PCA data to provide data representative of a corresponding modified head shape.

The system developed by Cranial Technologies required the use of trained operators to manipulate the captured data for a variety of reasons. Clinical adaptations to accommodate individual subjects and circumstances result in inconsistent orientations of the subject DSI® captured data files.

The trained operators view each DSI® captured data file of each subject and manually reorient the viewed image to a predetermined orientation. After manual reorientation, the operator manually selects the portion of the DSI® image data files for further use, thereby eliminating regions that will not be utilized.

The DSI® captured data file is then utilized by the Cranial Technologies system to produce a corresponding second data file representing the shape of a desired head shape. The corresponding second data file is then utilized to form an exact model of the desired head shape.

To form the cranial remodeling device, plastics material is drawn down onto the model of the desired head shape. After the plastics materials are drawn down onto the model, the plastics materials are cut along what are referred to as trim lines.

SUMMARY

In accordance with the principles of the invention, an improved method and system are provided for generating trim lines for a cranial remodeling device.

A method for manufacturing a custom cranial remodeling device of a type comprising plastic material is provided. The method includes the steps of: providing a first database of three-dimensional digital data of trim lines for cranial remodeling devices of a first type; providing a second database of three-dimensional digital data of trim lines for cranial remodeling devices of a second type; providing a first program for creating trim lines for a cranial remodeling device of the first type, the first program utilizing the first database; providing a second program for creating trim lines for a cranial remodeling device of the second type, the second program utilizing the second database; producing a three-dimensional model of a desired head shape; forming the plastic material onto the model; and selecting one of the first or the second programs to generate three-dimensional digital data of trim lines for the cranial remodeling device.

In one embodiment, the method further includes the steps of providing a first support vector machine; utilizing the first database to train the first support vector machine as the first program; providing a second support vector machine; and utilizing the second database to train the second support vector machine as the second program.

The method further includes generating a three-dimensional digital data file of the surface of the model having the plastic material thereon; and utilizing the selected one of the first or second programs to generate three-dimensional digital data for trim lines for the plastic material.

In the method, the trim lines comprise a top trim line and a bottom trim line. The trim lines further comprise a sidebar line.

In accordance with an aspect of the embodiment the method may comprise displaying the trim lines overlaid onto a three-dimensional digital surface image of the model having the plastic material thereon.

In one embodiment, the method comprises: generating a plurality of sets of trim lines for the plastic material; displaying the plurality of sets of trim lines overlaid on the three-dimensional digital surface image of the model having the plastic material thereon; and generating a plurality of sets of offset data each set corresponding to a corresponding one of the trim lines.

In an embodiment, the method comprises: generating each of the trim lines and the corresponding offset lines in an Initial Graphics Exchange Specification (IGES) format.

Further in accordance with an embodiment, the method comprises: selecting one set of trim lines of the plurality of sets of trim lines; and utilizing the corresponding set of offset lines to cut the plastic material Yet further in accordance with an embodiment, the method comprises: optimizing orientation of the three-dimensional digital surface image of the model having the plastic material thereon utilizing iterative differential evolution.

Still further in accordance with an embodiment, the method comprises: storing the generated trim lines in a corresponding one of the databases; and utilizing the corresponding one of the databases to retrain the corresponding one of the first or second support vector machines.

In one embodiment, the method comprises: generating a three-dimensional digital surface image of the model having the plastic material thereon; orienting the three-dimensional digital surface image utilizing iterative differential evolution to produce an oriented three-dimensional digital surface image; and scaling the oriented three-dimensional digital surface image utilizing Frobenius scaling.

An embodiment of a system for manufacturing a custom cranial remodeling device comprising plastic material is provided. The system of one embodiment comprises: a first database of three-dimensional digital data representative of trim lines for cranial remodeling devices of a first type; and a second database of three-dimensional digital data representative of trim lines for cranial remodeling devices of a second type. The embodiment further comprises one or more processors coupled to the first and second databases. A first program is executable by one processor of the one or more processors to create trim lines for a cranial remodeling device of the first type; the first program utilizes the first database. A second program is executable by one processor of the one or more processors to create trim lines for a cranial remodeling device of the second type; the second program utilizes the second database. The system further comprises first apparatus operable to generate a three-dimensional model of a desired head shape, and second apparatus operable to form the plastic material onto the model. The first and the second programs are selectively operable to generate trim lines on the plastic material formed onto the model to produce the cranial remodeling device.

In one embodiment, the first program comprises a first support vector machine trained with the first database; and the second program comprises a second support vector machine trained with the second database.

An embodiment of the system comprises three-dimensional image capturing apparatus operable to generate a three-dimensional digital surface image of the model having the plastic material thereon; and the one or more processors utilize the selected one of the first or second programs to generate trim lines for the plastic material.

One embodiment of the system comprises a display operable to display trim lines overlaid on the three-dimensional digital surface image of the model having the plastic material thereon.

Further in accordance with an embodiment, the one or more processors utilize the selected one of the first or second programs to generate a plurality of sets of data representative of trim lines for the plastic material.

Yet further in accordance with an embodiment, the one or more processors utilize the selected one of the first or second programs to generate a plurality of sets of offset data each corresponding to a corresponding one of the trim lines. The one or more processors generate each of the trim lines and the corresponding offset data in an Initial Graphics Exchange Specification (IGES) format.

Still further in accordance with the embodiment, the system is operable to select one set of trim lines of the plurality of sets of trim lines; and the system comprises apparatus operable to cut the plastic material in accordance with the trim lines and the corresponding set of offset data.

In a system in accordance with the embodiment, the one or more processors are operable to optimize orientation of the three-dimensional digital surface image of the model having the plastic material thereon. The one or more processors utilize iterative differential evolution to optimize orientation.

In a system in accordance with an embodiment, the generated trim lines are stored in a corresponding one of the databases; and the corresponding one of the databases is used to retrain the corresponding one of the first or second support vector machines.

In an embodiment of a system for manufacturing a custom cranial remodeling device comprising plastic material, the system comprises a first database comprising a plurality of three-dimensional digital data files captured directly from corresponding subjects; a second database comprising three-dimensional digital data files of modified head shapes each corresponding to one of the first data base digital data files; a third database comprising three-dimensional digital surface images of trim lines for cranial remodeling devices of a first type; a fourth database of three-dimensional digital surface images of trim lines for cranial remodeling devices of a second type. The embodiment further comprises one or more processors coupled to the first, second, third and fourth databases. The one or more processors utilizes the first, second and one of the third and fourth databases to fabricate a custom cranial remodeling device.

The embodiment of the system comprises a first program executable by one processor of the one or more processors to create trim lines for a cranial remodeling device of the first type, the first program utilizes the third database; and a second program executable by the one or more processors to create trim lines for a cranial remodeling device of the second type, the second program utilizing the fourth database.

The embodiment may further comprise first apparatus operable to generate a three dimensional model of a desired head shape; second apparatus operable to form the plastic material onto the model; and the one or more processors selectively operating the first and the second programs to generate trim lines for the plastic material formed onto the model to produce the cranial remodeling device.

In one embodiment the system comprises an operator viewable display, the one or more processors generate a three-dimensional image on the display of the plastic material formed on the model; and the one or more processors overlay one set of trim lines onto the three-dimensional image.

In an embodiment of the system each of the trim lines of the set of trim lines is displayed in a different color.

In an embodiment of the system the one or more processors generate a three-dimensional color topographic image on the display of the plastic material formed on the model.

The one or more processors overlay one set of trim lines onto the three-dimensional color topographic image.

An embodiment of the system further may comprise first apparatus operable to generate a three dimensional model of a desired head shape; and second apparatus operable to form the plastic material onto the model. The one or more processors selectively operate the first and the second programs to generate trim lines for the plastic material formed onto the model to produce the cranial remodeling device. The one or more processors generate offset data corresponding to each of the trim lines, the offset data is utilized such that a tool cutting the plastic material cuts perpendicular to the surface of the plastic material.

In a further embodiment, the one or more processors provide a spreadsheet function to input parameters for a milling machine carrying the cutting tool; and the one or more processors generates the offset data in accordance with the input parameters.

In yet a further embodiment, the one or more processors updates and adds to each of the first, second, and one of the third or fourth databases with each new custom cranial remodeling device.

In yet another embodiment of a system for manufacturing a custom cranial remodeling device comprising plastic material, the system comprises a first apparatus for directly capturing from a subject a three-dimensional digital data image file. The one or more processors are operable to manufacture a model of a desired head shape. Apparatus is provided to form one or more layers onto the model, the outer one of the layer comprising a copolymer. Additional apparatus directly captures a three-dimensional digital data image file from the model having the copolymer layer; and the one or more processors are operable to generate trim lines for the cranial remodeling device.

BRIEF DESCRIPTION OF THE DRAWING

The invention will be better understood from a reading of the following detailed description taken in conjunction with the drawing figures in which like designations are utilized to identify like elements, and in which.

DETAILED DESCRIPTION

Figure 1:
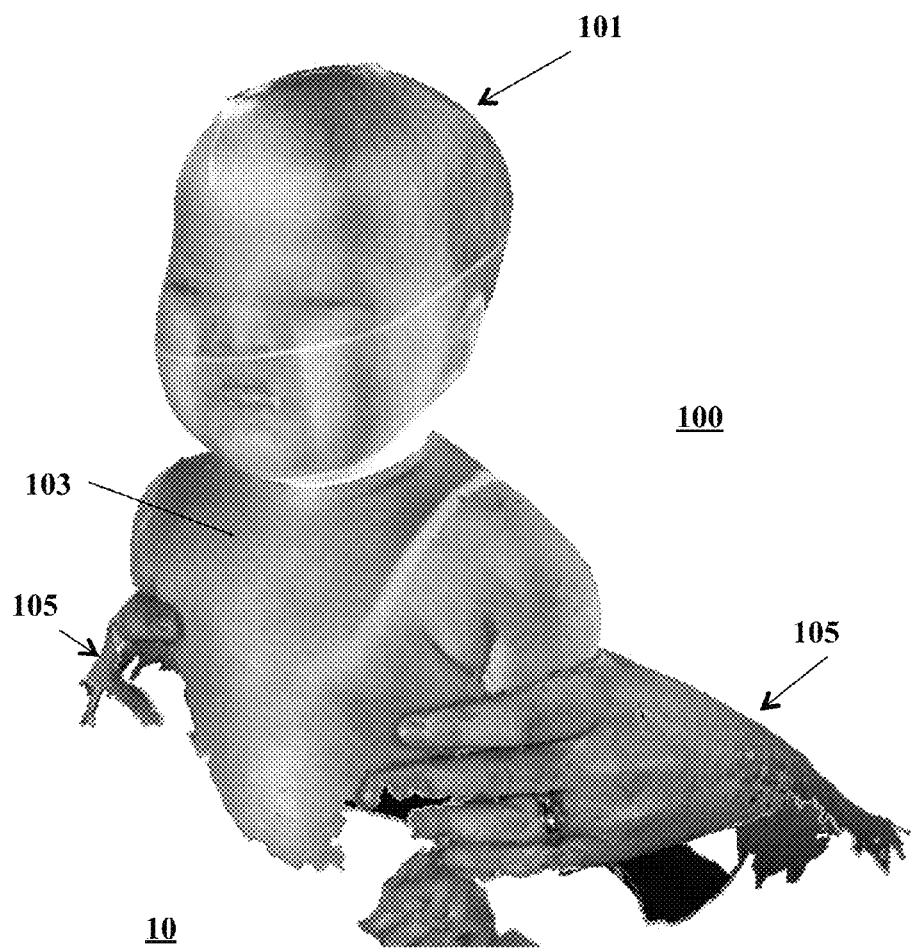
FIG. 1 illustrates a representative three-dimensional image with photographic overlay of a subject.

A library of hundreds of infant head casts and corresponding modified models has been maintained at the assignee of the present invention and this library of actual head casts and the corresponding modified models is believed to be a unique resource. It is this unique resource that was utilized to provide databases for developing the method and apparatus of the prior system.

Cranial Technologies, Inc. developed an image capture technology that has successfully replaced the traditional casting process. This technology referred to as the DSI® technology captures a 360-degree global image capture DSI® and provides improved surface detail over larger regions of the patient than achieved through casting.

Cranial Technologies utilized the DSI® system to capture three-dimensional images of plaster casts of patients' heads to develop a database that in turn was utilized to train a support vector machine.

Applicant recognized that the improved initial digital data record provided by the DSI® system presents an opportunity to provide an improved database, method and system in which three-dimensional digital image data captured directly from live subjects may be used to develop a new database and an improved system and methodology. Applicant has developed a new database, a new system, and new methodologies described herein that operate directly from image data captured directly from live subjects.

The DSI® system generates an image data file that is a digital mesh that represents the captured 360-degree global image. This image referred to as a DSI® mesh may be viewed on a monitor. In the past each DSI® mesh was manipulated by an operator.

In developing the database, system, and method of the invention, DSI® image data files captured directly from approximately 3,000 live subjects were utilized. These unaltered files, i.e., files that were neither oriented nor cropped, were selected to be representative files.

The DSI® image data files captured directly from subjects were utilized to construct a database utilized as described hereinafter.

U.S. Pat. No. 7,127,101 issued Oct. 24, 2006; U.S. Pat. No. 7,142,701 issued Nov. 28, 2006; U.S. Pat. No. 7,162,075 issued Jan. 9, 2007; U.S. Pat. No. 7,177,461 issued Feb. 13, 2007; U.S. Pat. No. 7,227,979 issued Jun. 5, 2007; U.S. Pat. No. 7,242,798 issued Jul. 10, 2007; U.S. Pat. No. 7,245,743 issued Jul. 17, 2007; U.S. Pat. No. 7,280,682 issued Oct. 9, 2007; and U.S. Pat. No. 7,305,369 issued Dec. 4, 2007 are all assigned to the assignee of the present application and the disclosures contained in each of the patents are expressly incorporated herein by reference.

U.S. patent application Ser. No. 12/383,198 filed Mar. 20, 2009 and published as Publication No. 2010/0239135A1 on Sep. 23, 2010; and Ser. No. 12/798,076 filed Mar. 29, 2010 and published as Publication No. 2010/0238273A1 published on Sep. 23, 2010 are all assigned to the assignee of the present application and the disclosures contained in each of the applications as published are expressly incorporated herein by reference.

The DOC Band® or side-opening type is used primarily to treat children with plagiocephaly, or asymmetrical head configurations. It applies forces in a typically diagonal fashion. A representative side-opening band is described in U.S. Pat. No. 5,094,229 which is incorporated herein by reference.

In the following description, the style of band or device includes: RSO or right side opening cranial remodeling device and LSO or left side opening cranial remodeling device.

Figure 2:
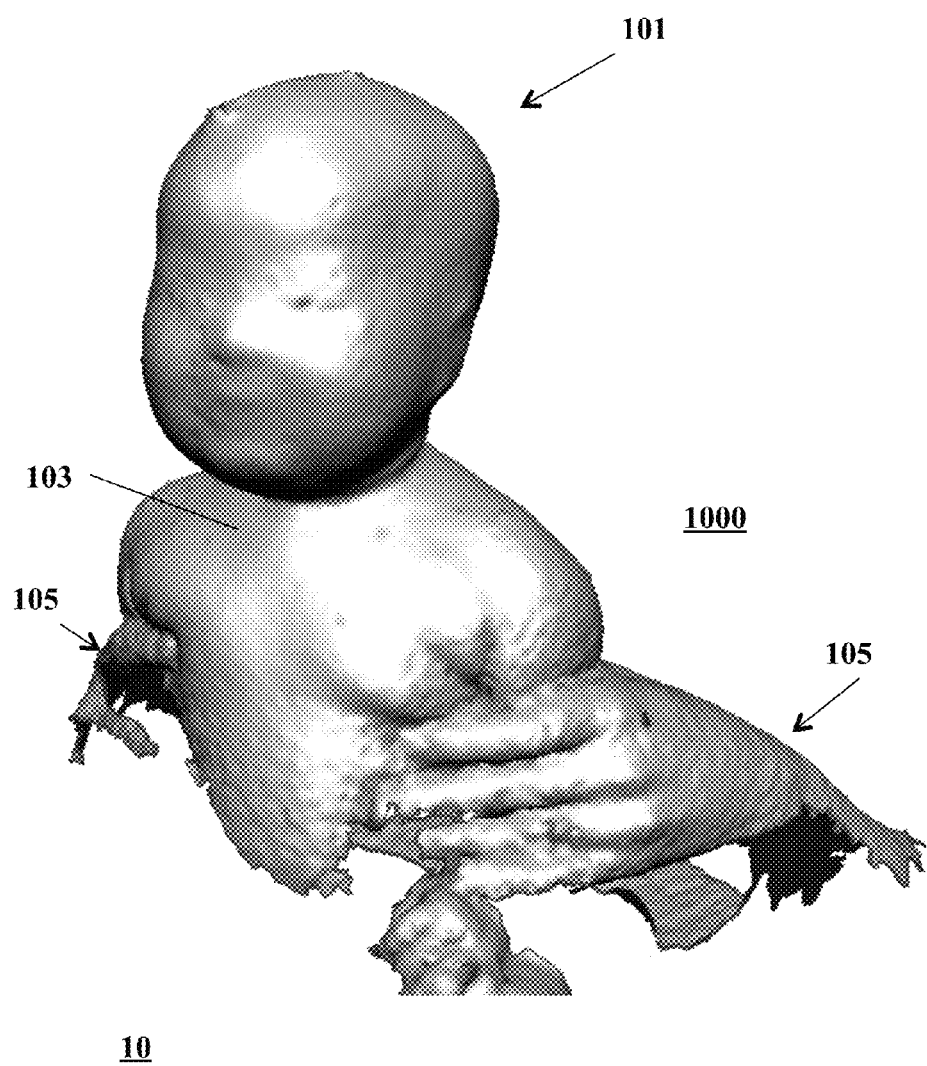
FIG. 2 illustrates the three dimensional image of FIG. 1 without the photographic overlay.

Turning now to FIGS. 1 and 2, a typical DSI® data file 10 captured from a live subject. FIG. 1 shows an operator viewed image 100 of data file 10 with a photographic overlay, and FIG. 2 illustrates a viewed image 1000 of data file 10 without photographic overlay. For a variety of reasons, the orientations of data files 10 and the corresponding images 100, 1000 vary significantly from subject to subject. Also, as is apparent from FIGS. 1 and 2, the captured image data includes not only the head 101, but the chest 103 of the subject and if the subject is held in position, the hands 105 of the holder of the subject.

Figure 3:
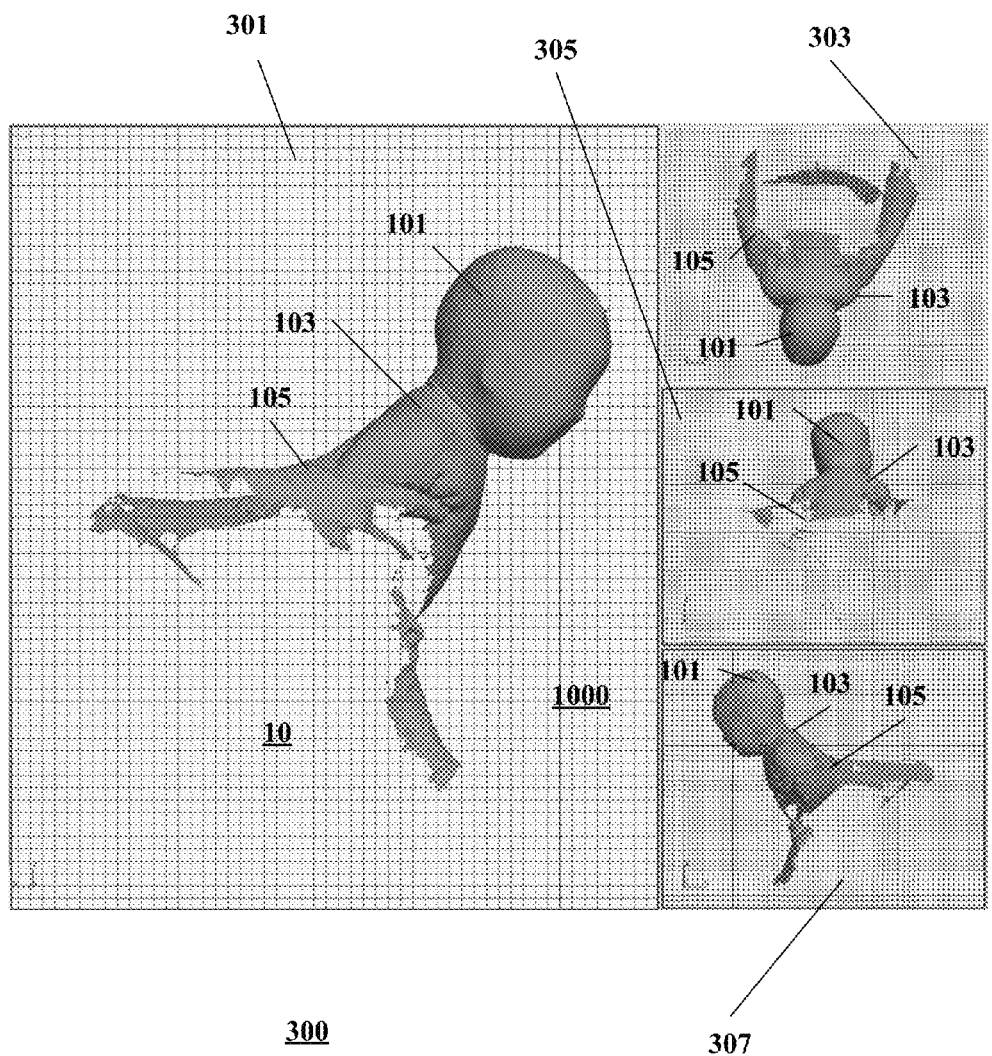
FIG. 3 is a first screen shot of a display.

Turning to FIG. 3, a typical screen-shot displaying different views of a data file 10 is shown. Screen-shot 300 includes a right side view 301, top view 303, rear view 305 and left side view 307.

Captured DSI® data for different subjects are not aligned with each other. Accordingly captured DSI® data for a plurality of subjects cannot simply be averaged together. The captured DSI® data for different subjects must be properly scaled and oriented before averaging can be effective.

One method for registering images and digital records of anthropological artifacts is known as the "Procrustes method". It applies where a group of similar but individually unique items needs to be consistently described or processed. The Procrustes method as it is referred to in the scientific literature is simply resizing and alignment of each element in the database to match the orientation and size of the average element of the database. The fundamental difficulty encountered is that the average element of the database is not known before the alignment process begins.

In an embodiment of the invention, a "Procrustes" type of registering of data files in a database is provided.

Figure 4:
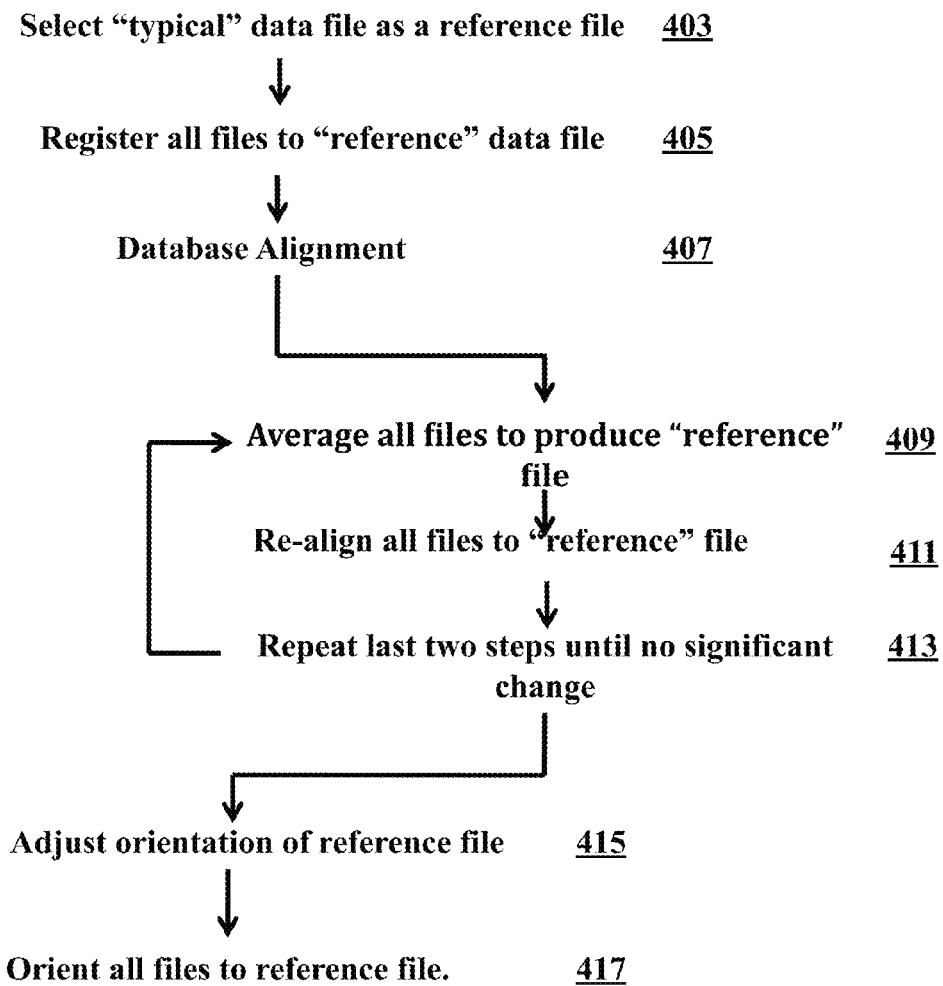
FIG. 4 illustrates steps utilized in one embodiment.

As shown in FIG. 4, database alignment shown at step 407 is preceded by first selecting as a reference mesh, a "typical" or "reference" subject DSI® data file 403 from the database and registering all of the other DSI® data file to the "reference" file at step 405.

Registration occurs by changing the seven parameters on the DSI® data mesh until a metric measuring the alignment of the two meshes is optimized. Registration optimization is obtained in two separate steps: a coarse registration followed by a fine registration. The coarse registration employs a robust metric and brings the two objects close enough together so that the sensitive metric employed by the fine registration can succeed to produce a more exact result. After this initial alignment is performed, all DSI® data files in the database become more closely aligned.

To simplify the math the six orientation parameters of a reference mesh are all set to zero. As a consequence, only the six parameters for the DSI® mesh are needed to align the two meshes. Adding a single magnification or scale parameter then brings the total number of parameters to seven. Magnification of the reference is taken as 1.0. Orientation of DSI® data meshes to the reference mesh is accomplished by specifying six parameters: one translation (distance from the origin) for each of the three coordinate axes and one rotation around each coordinate axis. Aligning two DSI® meshes requires specifying the six parameters for each DSI® mesh so that the two DSI® meshes will be in the same spatial location and orientation.

Database alignment 407 is then performed by first averaging the more closely aligned files at step 409 to produce a new reference file. Each DSI® data file is then re-aligned to the new reference file at step 413. The result is that all the files are brought into even better alignment because the new average was more typical than the original DSI® reference. This averaging and re-alignment processing steps 409, 411 are repeated the reference DSI® data file produced does not change significantly with repeated processing.

Final orientation of DSI® data meshes is achieved after automated alignment and cutoff of each new DSI® data mesh as described below. An alignment algorithm registers each new DSI® data mesh to the database reference independent of the orientation of the reference. By adjusting the orientation of the reference, each new DSI® data mesh is automatically oriented as well as registered. The final orientation can be adjusted at any time.

Although human vision systems easily recognize general similarities between objects, mathematical registration does not. We developed an approach to automatically provide registration.

In the following description of registration of two meshes, the first of the two meshes is referred to as the "library" or "reference" mesh and the second mesh is referred to as the DSI® mesh.

The system and method described herein operate on a three-dimensional digital image of a subject that is in a predetermined format. The system and method automatically crop and orientate the digital image to be consistent with a library reference. Four crops of the digital mesh are automatically provided to yield a digital mesh that is stored in a database and that is used for further processing.

The system may be operated such that at least some of the crops and orientating are provided with operator control and/or intervention.

Representative methodology utilized in various embodiments is first summarized below with respect to the method steps of FIG. 5 and a representative vertex point cloud 600 for the subject of FIGS. 1 and 2 shown in FIG. 6.

In an initial step 501, extraneous information, i.e., stray polygons and vertices, is removed. Removal of unattached vertices and other mesh elements is achieved using a commercially available software function on an adjacency matrix defined by the DSI® mesh. This operation leaves intact only the largest "connected" section of the mesh.

Figure 6:
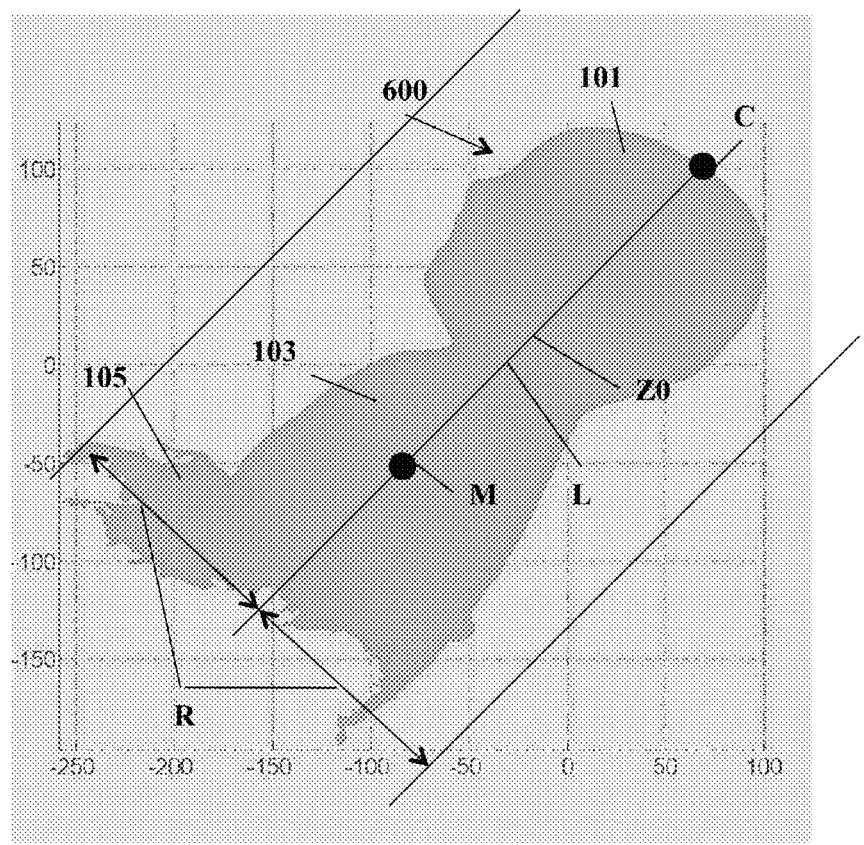
FIG. 6 illustrates a vertex cloud for determination of a reference axis for an image of FIG. 1.

After removal of the extraneous information, two points are selected for the vertex point cloud 600 of the subject at step 503 as shown in FIG. 6. The median M of vertex point cloud 600 is determined. The median M of vertex point cloud 600 is independent of the orientation of cloud 600. For the DSI® captured data files, the median M is almost always approximately in the center of the chest cavity.

The furthest point C away from the median but lying such that both its z-axis coordinate and y-axis coordinate are positive is identified. Point C is on the upper cranium.

The line L joining the median M and this furthest point C is taken to be a new z-axis Z0 at step 505. The other axes, i.e., x-axis and y-axis, are computed easily since they are orthogonal to z-axis Z0.

Once axis Z0 is identified, a first crop is performed at step 507 to remove all portions of the image that are more than a first predetermined radial distance R away from axis Z0. The radial distance selected in the illustrative embodiment is selected to be 150 cm.

Figure 7:
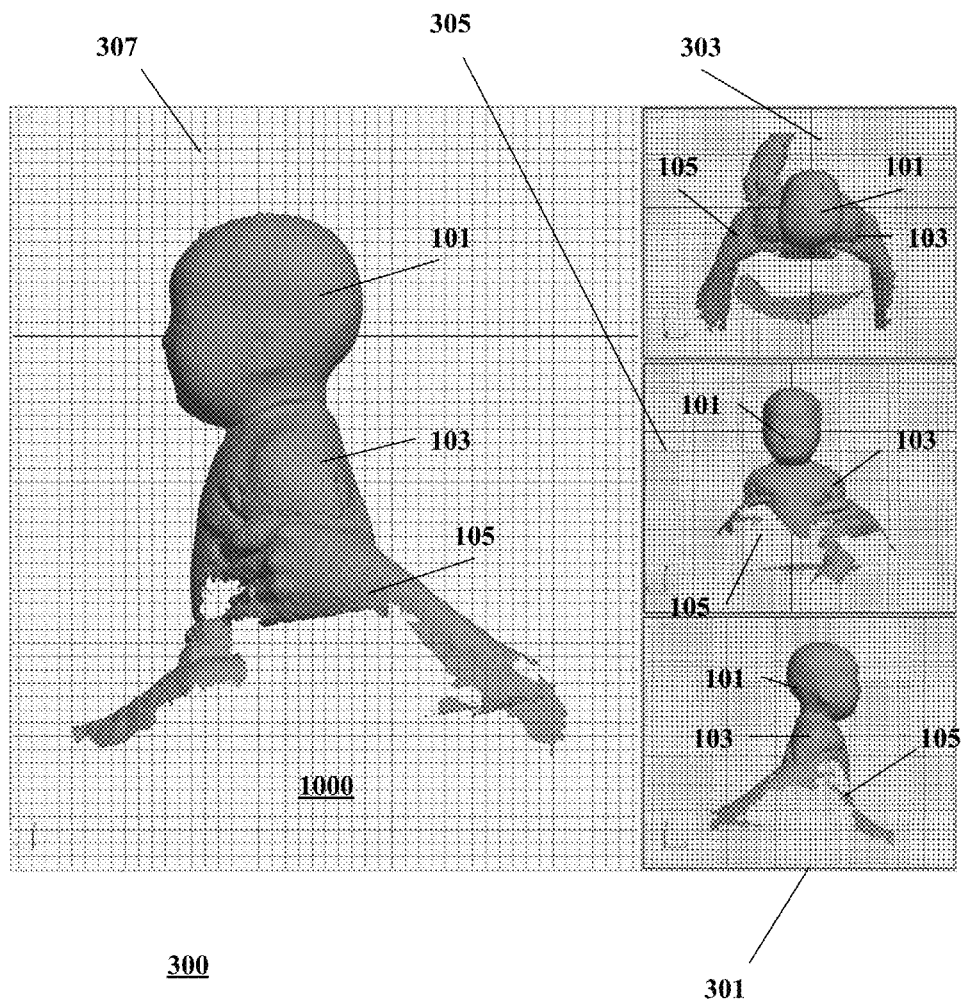
FIG. 7 is a second screen shot of a display showing the image re-oriented to a reference axis.

Axis Z0 is utilized to orient image 100 consistent with the reference. The reorientation produces the reoriented images as shown in the screen shot of FIG. 7.

Figure 5:
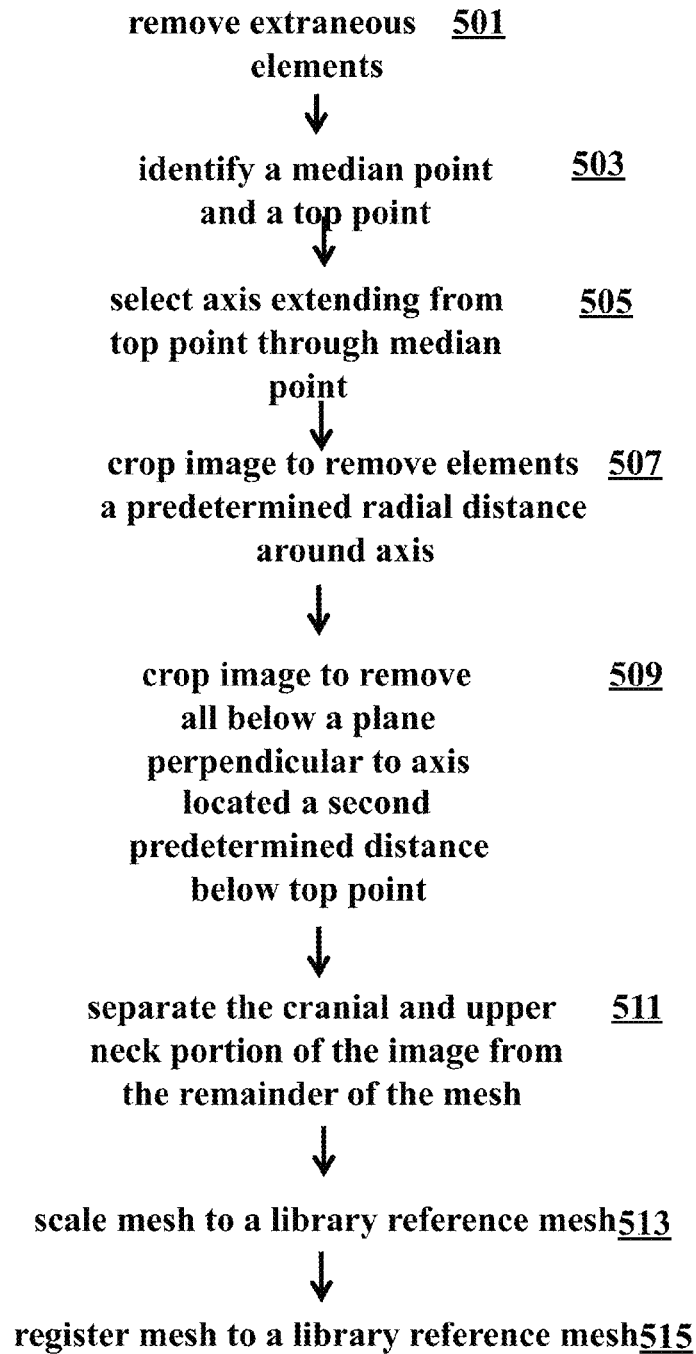
FIG. 5 illustrates further steps utilized in an embodiment.
Figure 8:
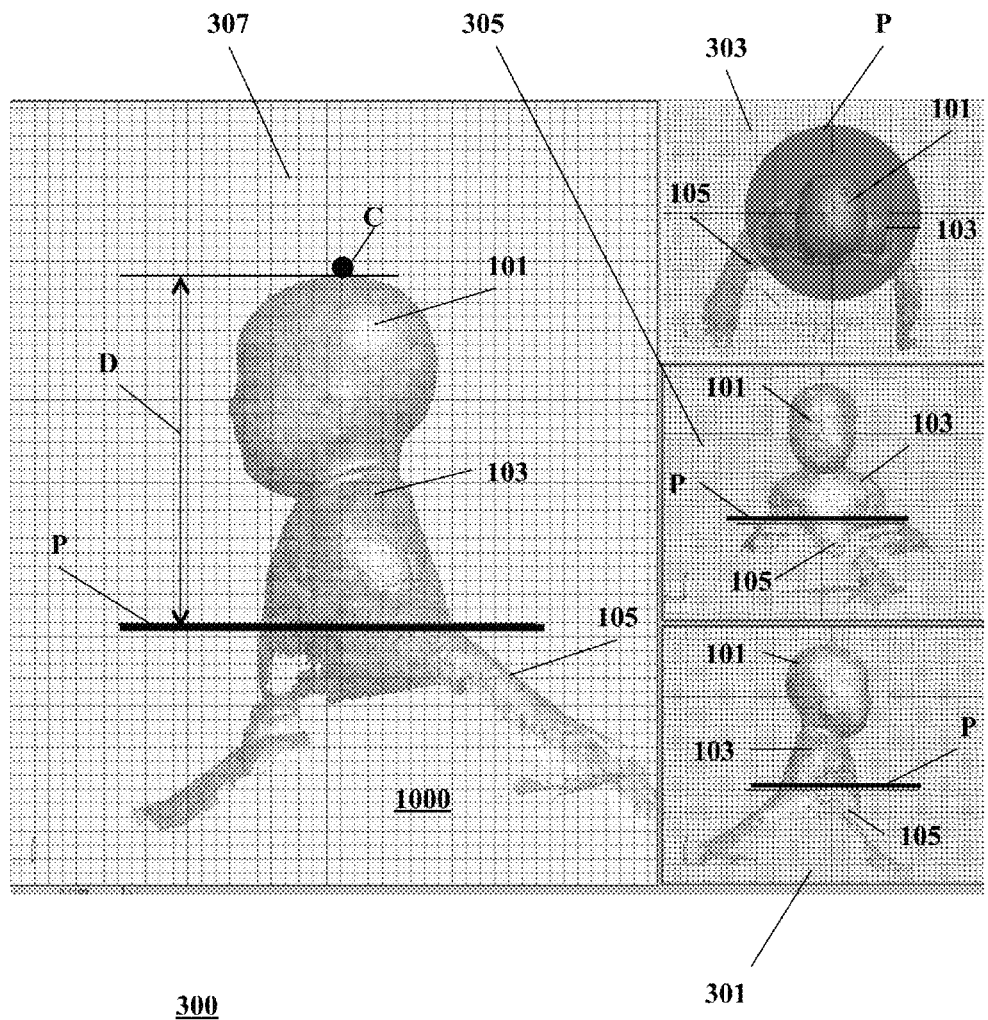
FIG. 8 is a third screen shot of a display showing the location of a cropping plane.

A second crop is performed at step 509 as shown in FIG. 5. A plane P is selected at a second predetermined distance from the second point C as shown in the screen shot of FIG. 8. Plane P is selected to be perpendicular to axis Z0. All portions of the DSI® data mesh 1000 that lie below plane P are cropped out or removed.

Figure 9:
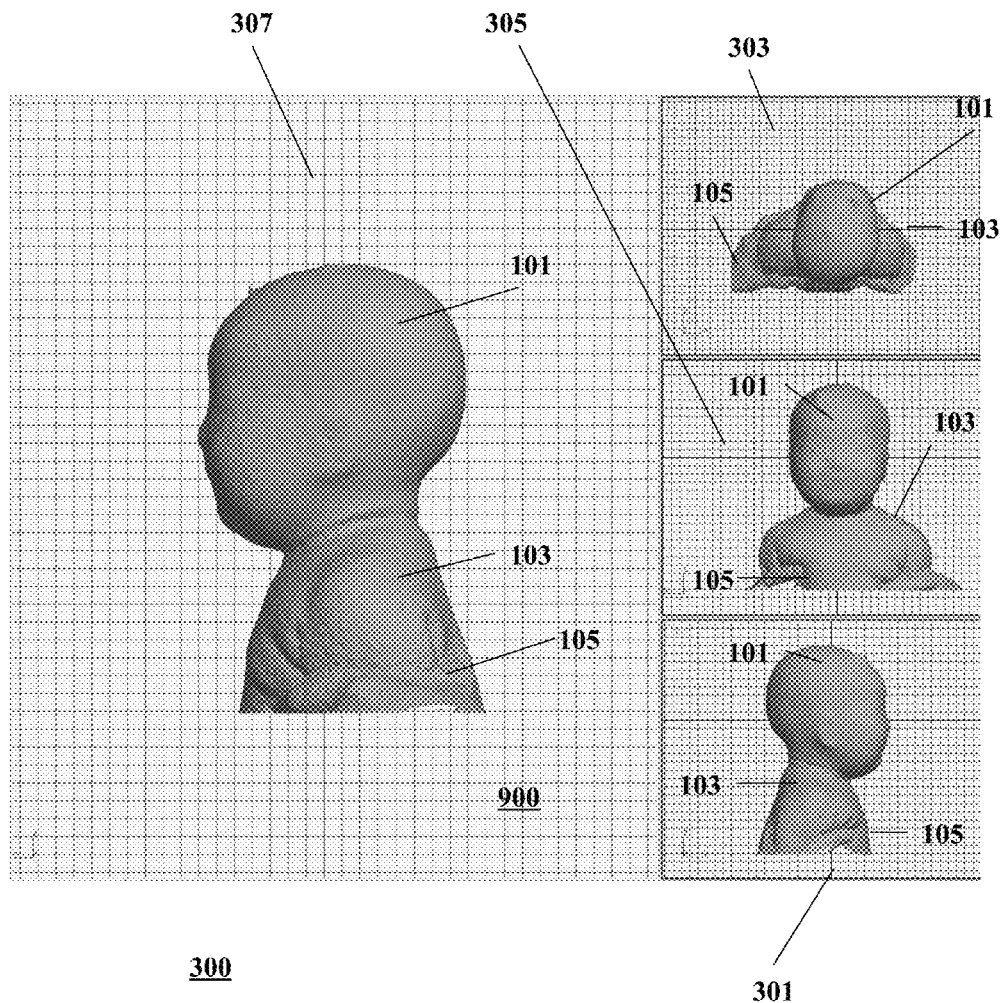
FIG. 9 is a fourth screen shot after a first crop.

The resulting data mesh 900 shown in the screen shot of FIG. 9 comprises the cranium 101 and the upper chest portion 103, 105 of the subject DSI® data mesh 1000. This final "cranial mesh" 900 contains fewer vertices and fewer triangles than the original DSI® mesh.

Turning back to FIG. 5, at step 511 the cranial and upper neck portion of the DSI® data mesh is separated from the remainder of the mesh. A predetermined algorithm is utilized to separate the cranial and upper neck portion of the image from the remainder of the mesh. The predetermined algorithm utilized in the embodiment of the invention is a mixture of Gaussians (MOG) algorithm.

The remaining mesh containing primarily the chest and cranial regions, is analyzed using MOG to identify each vertex as lying in one of two classes. One class normally contains only the upper neck and cranial region, the other class has the rest of the chest mesh. This neck/cranial region is entered into a coarse registration. After using a "Procrustes" function on the geodesically determined vertices, all further registrations are based on predetermined points selected in the cranial region of the "chest mesh". Using the chest mesh in later registration rounds allows more of the neck region to enter the registration if needed, but using only the cranial region for the initial 512 vertices better concentrates those and all later selections within the cranium.

Figure 10:
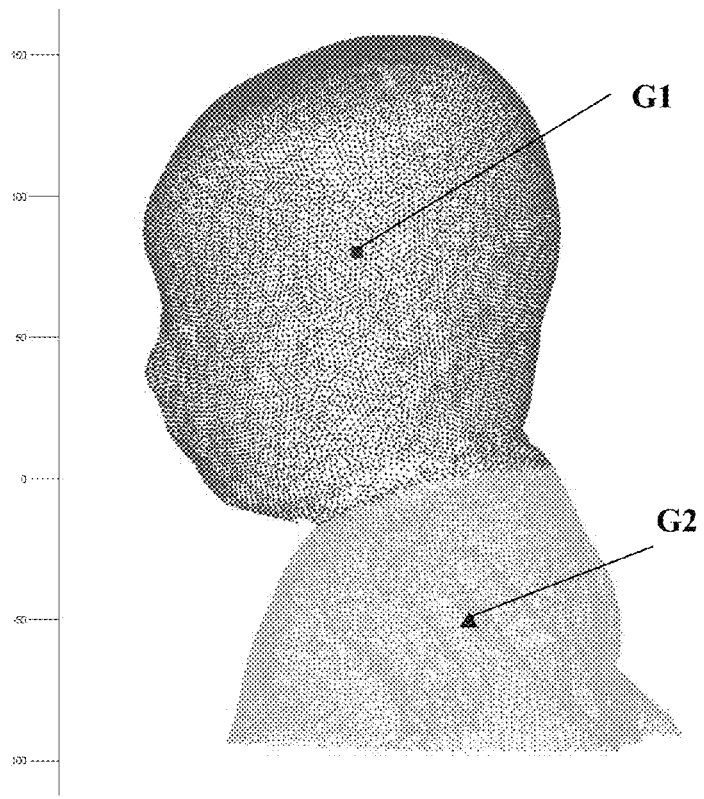
FIGS. 10 and 11 illustrate the location of Gaussian weighted centers of the head and chest portions of the images of FIG. 9.
Figure 11:
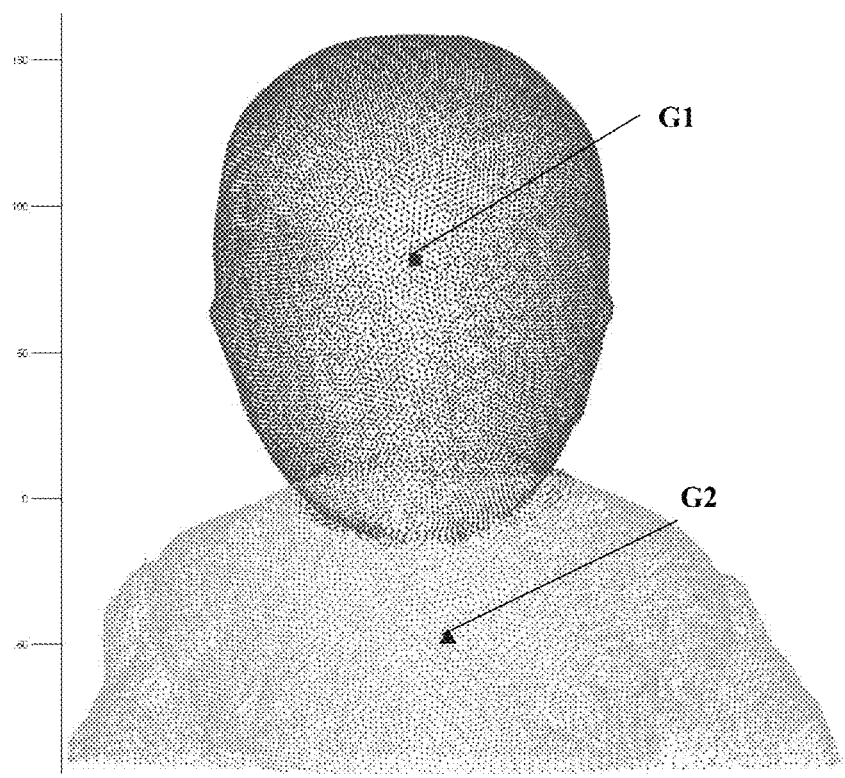
Figure 12A:
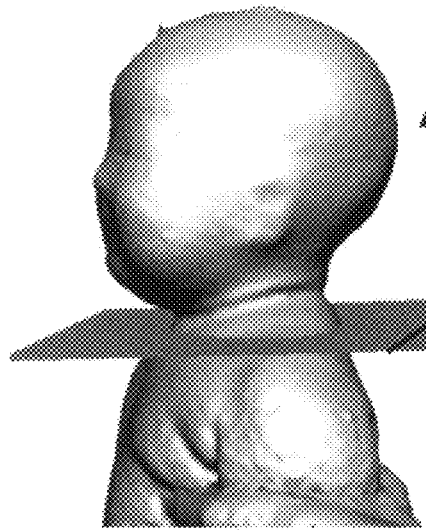
FIGS. 12A, 12B, 12C, and 12D illustrate the position of a second cropping plane from the left side, front, back and rear side.
Figure 12B:
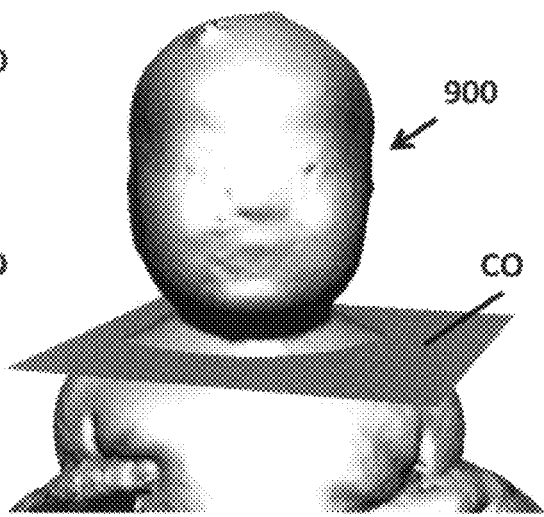
Figure 12C:
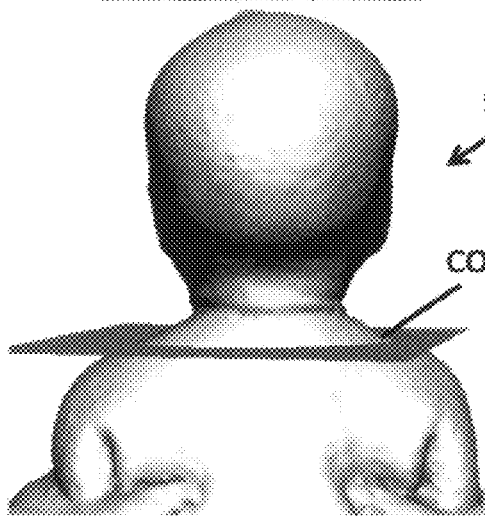
Figure 12D:
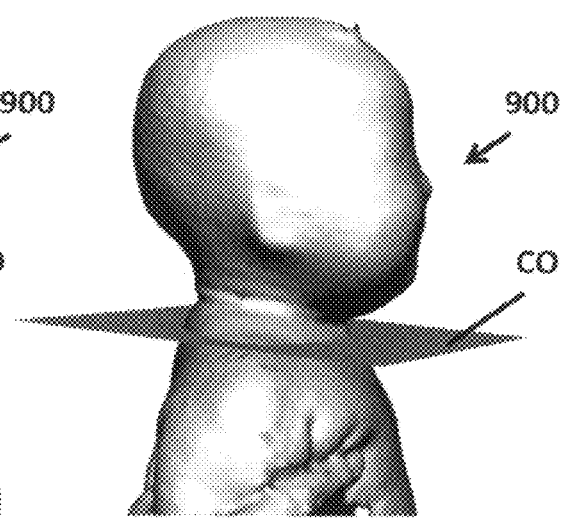

FIGS. 10 and 11 illustrate the locations of a calculated MOG cranium center G1 and a calculated chest MOG point G2. Utilizing MOG points G1, G2, a crop plane C0 is determined as shown in FIGS. 12A, 12B, 12C, and 12D.

Figure 13:
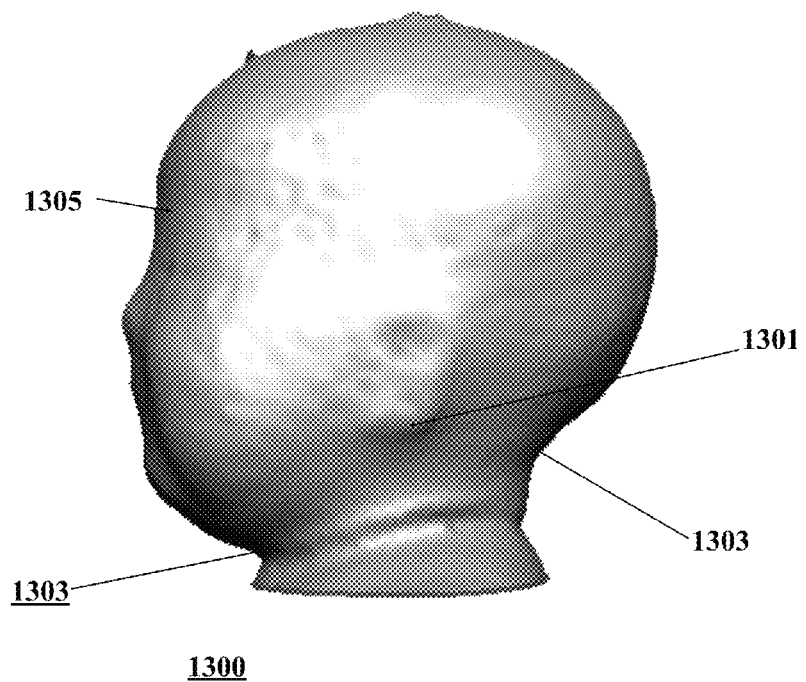
FIG. 13 illustrates a view of the three-dimensional image after a second cropping.

DSI® data mesh 900 is cropped to remove the mesh portion lying below crop plane C0 producing the DSI® data mesh 1300 shown in FIG. 13.

Turning back to FIG. 5, the resulting DSI® data mesh image 1300 is then scaled to a library reference mesh based upon the shape of the cranium utilizing Frobenius metrics to determine a scale factor to the library reference mesh as indicated at step 513.

Following scaling, the resulting DSI® data cranial mesh is registered at step 515 to the library reference mesh utilizing a two-step translational registration using least squares followed by mutual information. The resulting. DSI® data cranial mesh 1300 is stored in a database for further processing.

In a second embodiment, the cranial mesh is further operated on to identify those portions of the mesh 1300 that are of particular interest for further processing.

In this embodiment, further cropping of the image mesh is provided.

In the particular application of the system and method of the invention, the portion of the subject below the bottom of the ear lobes is not of relevance.

In particular, portions of the DSI® data cranial mesh that are not necessary for further processing are cropped off the image mesh.

Figure 14:
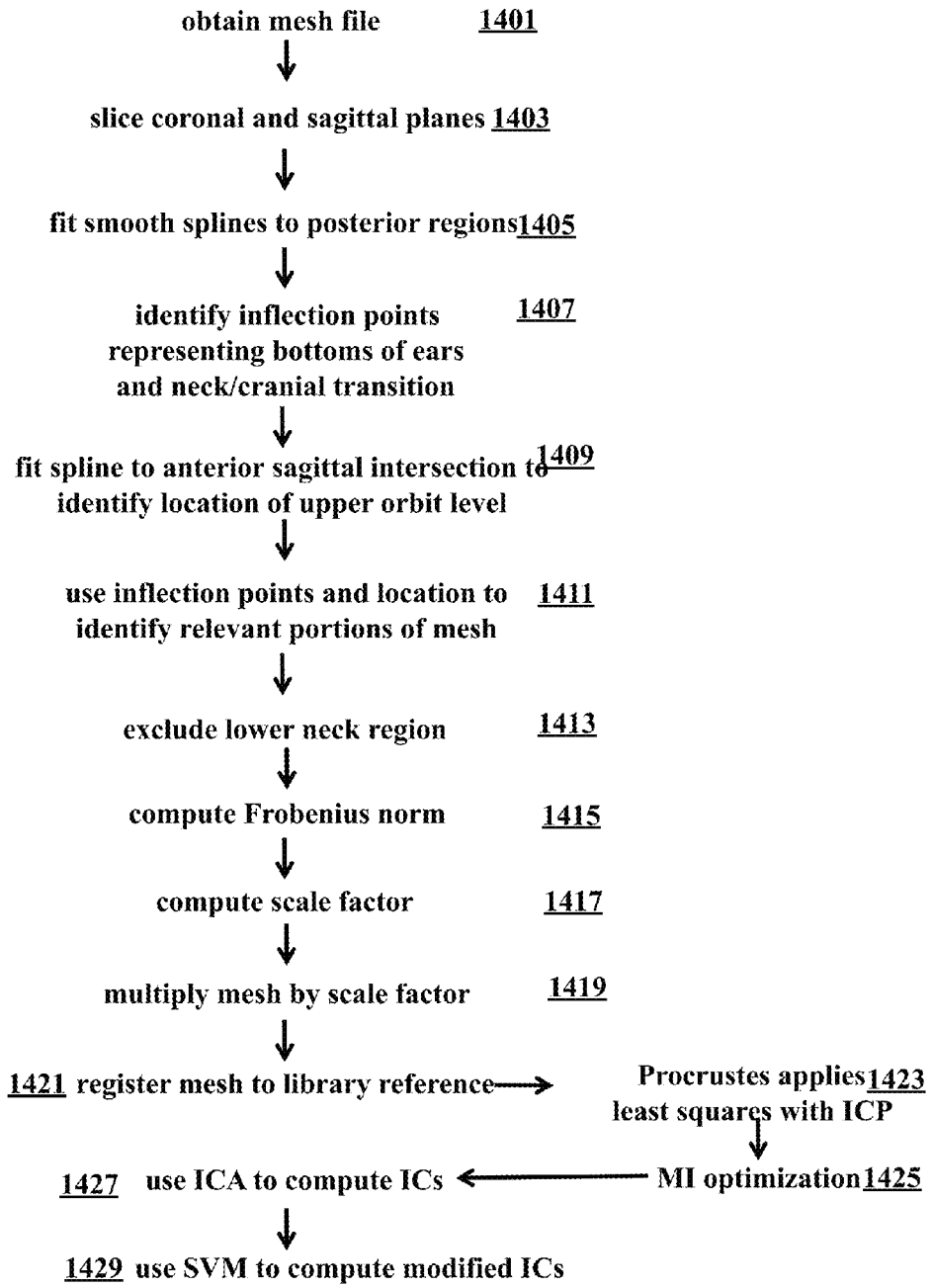
FIG. 14 illustrates a further methodology steps.

Turning now to FIG. 14, the additional steps that are utilized are described.

At step 1401 the DSI® data cranial mesh 1300 is obtained from the database.

Key inflection points are identified on the mesh image to locate the orbits of the subject and to identify the bottoms of the ears of the subject. Key inflection points in the embodiment are determined by first slicing the DSI® data cranial mesh through coronal and sagittal planes as indicated at step 1403. Smooth splines are fit to posterior regions at step 1405. Inflection points are identified representing the bottoms of the ears 1301 and the neck/cranial transitions 1303 at step 1407.

A spline is fit to the anterior sagittal intersection of the planes to identify the location of the upper orbit level 1305 at step 1409.

After key inflection points 1301, 1303, 1305 are identified, the inflection points are utilized to identify relevant portions of the DSI® data cranial mesh 1300 at step 1411.

Figure 15:
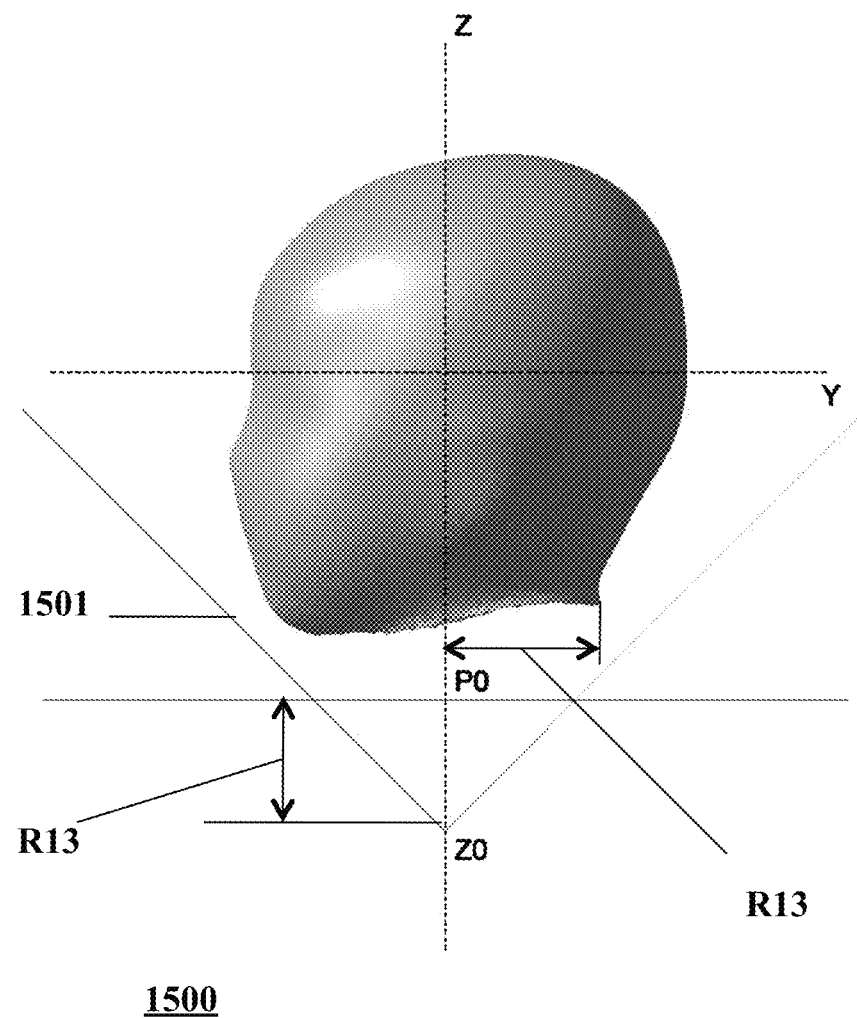
FIG. 15 a cropping configuration.

The identification of the bottoms of the ears is utilized to identify a further crop plane that is used to exclude that portion of the DSI® data cranial mesh below the plane to exclude or crop off the lower neck region from DSI® data cranial mesh at step 1413 to produce the digital mesh 1500 shown in FIG. 15.

Subsequent to cropping the DSI® data cranial mesh 1300, Frobenius scaling is again applied to produce a cranial mesh. Frobenius scaling is accomplished by computing a Frobenius norm at step 1415 and then computing a scale factor at step 1417. The DSI® data cranial mesh is then multiplied by the scale factor at step 1419.

After the Frobenius scaling, the cranial mesh is registered to the reference mesh at step 1421 by utilizing translational registration using least squares. A "Procrustes" function is used to apply least squares with iterative closest points computed by normal shooting, i.e., bed of nails, at step 1423. The Procrustes function step is followed by mutual information (MI) with pattern search optimization at step 1425. All rotational degrees of freedom remain unchanged, only the translational degrees are optimized.

After isolating cranium mesh CM and defining a new z-axis Z0, additional coarse registration is performed using an Iterative Closest Points (ICP) algorithm. The ICP algorithm operates by selecting a set of points on the reference and locating the closest set of matching points on the cranial mesh. A set of transformations is applied and the registration quality metric is computed for each of the transformations. Once the optimal transformation according to the metric is identified and applied to the cranial mesh, the matching of cranial mesh points to those on the reference is repeated. Because the cranial mesh location has been transformed, the new matching set is different than the previous matched set and so the transformation optimization is again optimized and the closest matching set of points identified. These iterations continue until the transformations are acceptably small.

Figure 16:
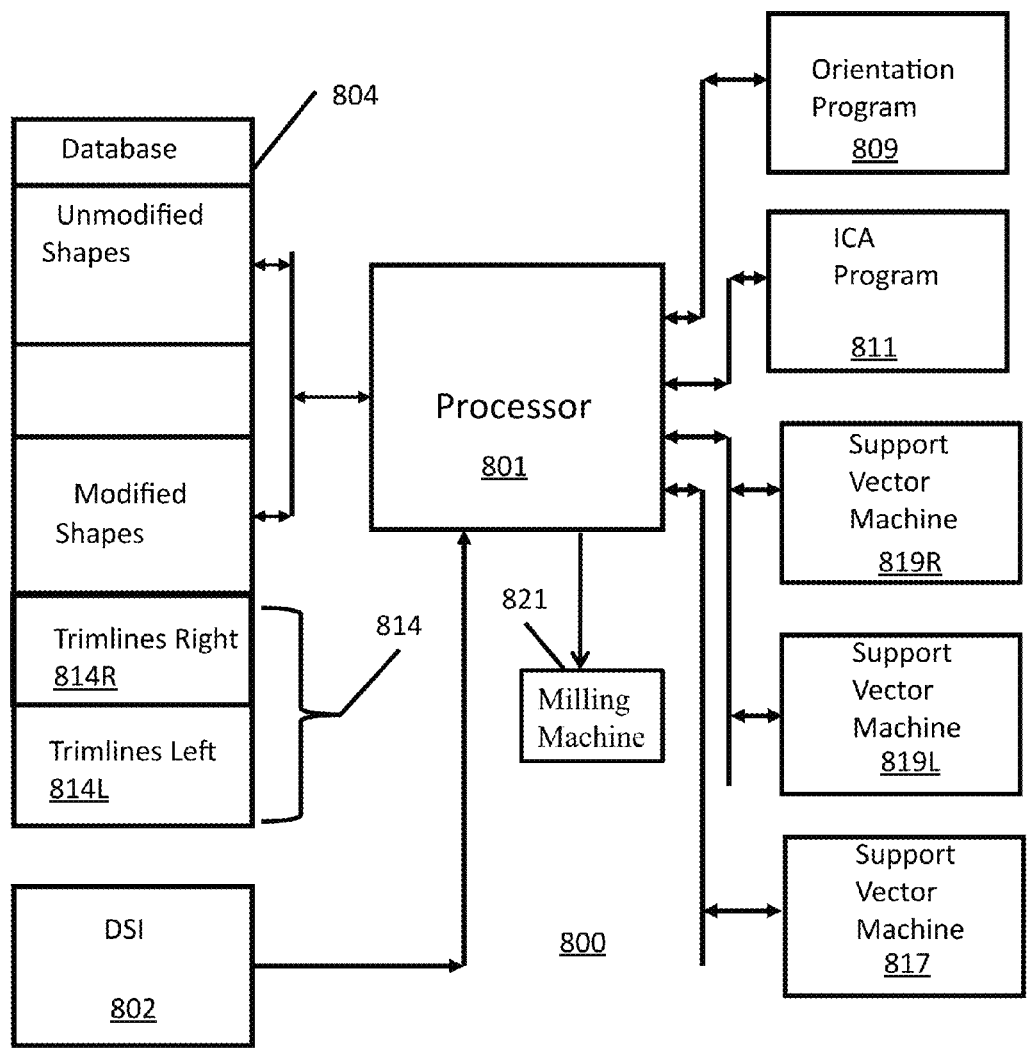
FIG. 16 is block diagram of a system.

Turning now to FIG. 16, system 800 utilizes the methodologies described above. System 800 comprises a computer or processor 801 that processes DSI® files received from DSI® system 802. A plurality of DSI® files are stored in database 804. The database 804 files are used to train a Support Vector Machine (SVM) 817. Support Vector Machine 817 is an application that processes each DSI® file to output a properly oriented and "modified" stereo lithography (STL) standard file replicating a modified shape that would have previously been produced by a trained expert.

STL is a file format native to stereo lithography CAD software that is commercially available. STL files describe only the surface geometry of a three dimensional object without any representation of color, texture or other common CAD model attributes. An STL file describes a raw unstructured triangulated surface by the unit normal and vertices of the triangles using a three-dimensional Cartesian coordinate system System 800 automatically processes digital image representations representative of a subject head shape. System 800 comprises a database library 804 of a first plurality of first three-dimensional DSI® digital data file image representations of subject head shapes captured directly from live subjects, and a second plurality of second three-dimensional DSI® digital data file digital image representations of corresponding modified head shapes. System 800 includes processor 801 that further comprises a support vector machine application 817. Database library 804 is used to provide the plurality of said first and second three-dimensional DSI® digital data file digital image representations to processor 801 to train support vector machine 817 to operate on new three-dimensional DSI® digital data file digital image representations.

System 800 receives a new three-dimensional DSI® digital data file digital image representation file or DSI® mesh of a subject head shape from DSI® system 802. Support vector machine 817 operates on the DSI® mesh to generate a corresponding new second three-dimensional DSI® digital data file image representation replicating a corresponding modified head shape and stores each new three-dimensional DSI® digital data file image representation and the corresponding new second three-dimensional DSI® digital data file image representation in database 804.

In accordance with the methodology described hereinabove, processor 801 operates on a raw file received from DSI® system 802. Processor 801 removes all vertices, polygons, or other mesh elements that are not attached to the subject. Processor 801 analyzes the resulting point cloud of the retained mesh using k-means. This provides two "centers", one for the vertices labeled to be in the upper mesh and the other for vertices labeled to be in the lower mesh. A line joining the upper and lower centers defines an initial vertical z-axis for the patient. A patient y-axis is computed as the cross product of this patient z-axis with the original x-axis provided by the digitizer. A new patient x-axis is finally computed as the cross product of the patient y-axis and z-axis. The mesh is rotated into this initial "patient coordinate system". In the patient coordinate system a "chest cutoff" is applied to produce the "chest mesh". For this, mesh elements less than 250 mm from the highest point of the mesh and lying within 150 mm of the z-axis are retained. A mixture of Gaussians (MOG) algorithm is then applied to separate the cranial and upper neck region from the rest of the chest mesh.

The median of the remaining cranial mesh is subtracted from each vertex in order to center at a new origin of coordinates. This median is computed using an area-weighted statistical sampling of the mesh. This sampled median approach overcomes non-uniformly spaced vertices produced.

Processor 801 then operates on each new three-dimensional DSI® digital data file image representation or DSI® mesh to orient said new digital image representation consistent with the three-dimensional DSI® digital data file image representations or DSI® mesh information stored in database 804. After orienting, processor 801 cuts or crops the DSI® mesh to obtain a corresponding cranial mesh.

After obtaining a corresponding cranial mesh, system 800 processes the cranial mesh to generate a new three-dimensional DSI® digital data file image representation or modified three-dimensional DSI® digital data file representative of a desired head shape.

System 800 updates database 804 by storing each new first three-dimensional DSI® digital data file image representation or DSI® mesh in the database library 804 with the first plurality of first three-dimensional DSI® digital data file image representations and storing each corresponding new second three-dimensional DSI® digital data file image representation.

System 800 utilizes the updated database 804 to retrain support vector machine 817.

Independent Component Analysis (ICA) application program 811 initiates an ICP algorithm by selecting predetermined number vertices geodesically spaced on the reference model and then mathematically projected onto a unit sphere, i.e., a sphere centered at zero and having a radius of 1.0. Vertices from a cranial DSI® mesh are also projected onto the unit sphere and those lying closest to the set of the predetermined number of vertices projected from the reference model were selected to initiate the ICP algorithm.

The metric used to assess registration quality is sensitive enough to distinguish between small movements, but robust enough to achieve good results with the large variety of shapes presented by the raw cranial meshes.

After all subject files in database 804 are registered to the reference mesh, the average of the DSI® cranial meshes is taken to generate an updated reference mesh and continue the Procrustes averaging Turning back to FIG. 14, shapes computed by ICA are applied to the DSI® data cranial mesh at step 1427. A predetermined set of 128 independent components, IC, was found to allow very satisfactory representation.

The cranial mesh represented using ICA shapes is applied to a support vector machine (SVM) 817. SVM 817 uses the cranial mesh IC's as input and computes modified IC's as its outputs at step 1429.

The modified IC's define a cranial mesh for a modified head shape. The cranial mesh for the modified head shape is utilized to fabricate a custom cranial device.

To prepare for the first rounds of Iterated Closest Points (ICP) two preliminary steps are performed. A search tree for the cranial mesh is built and a "unit sphere matching" is performed. The search tree speeds the process of identifying which points in the cranial mesh lie closest to those in the reference mesh set. Given the index of a point or set of points in the reference mesh set, ICP requires identifying the index of the closest point in the cranial mesh. This tree simply speeds the searches for the closest points. The "unit sphere matching" is done to initiate the ICP.

Each vertex of the re-centered DSI® mesh is projected onto the unit sphere by dividing the vertex vector by its own magnitude. A set of 512 vertices is established on the reference mesh. That set of vertices is geodesically spaced on the reference mesh and their indices are stored in database 804. Projecting them onto the same unit sphere as the re-centered cranial mesh allows identifying the set of cranial mesh vertices that are closest to the geodesic set from the reference mesh. This matched set and the search tree are used to do a predetermined number of rounds of ICP using a "Procrustes" function.

Fine registration differs from the coarse registration in three significant ways. First, the reference mesh is treated as a surface rather than just a collection of geodesically spaced vertices. Second, the set of vertices used in the cranial mesh do not change; they are the ones from the final match achieved in the coarse registration. The third difference is that only MI optimization is done, no preliminary ICP is applied.

Processor 801 averages all of the cranial meshes together to establish a reference mesh.

Once processor 801 aligns all of the cases in database 804, processor 801 computes the trimmed mean of each vertex. The trimmed mean throws away the most extreme 30 percent of the cases at each vertex and computes a uniformly weighted average of the remaining cases.

Processor 801 applies averaging separately to the x, y, and z coordinates to generate a "right side" flattened average mesh. The right side mesh is then mathematically mirrored about its x-axis and averaged with itself to create a symmetric reference mesh.

Processor 801 uses the symmetric reference mesh to compute other information stored in database 804 to define the coordinate system for a "cone" used in a final cropping. This crop is achieved using a truncated and inverted cone 1501 as shown in FIG. 15. The axis z of the cone 1501 is aligned with the vertical axis and its wall is at 45 degrees from the vertical. The mesh elements lying above a horizontal plane P0 disposed orthogonal to cone axis Z and the inside inverted cone 1501 are retained as the final mesh; those outside of that region are discarded.

Database 804 also contains three-dimensional DSI® image data files 814 for each cranial remodeling device corresponding to each three-dimensional DSI® image data file for an unmodified head shape and its corresponding modified head shape utilized to produce each model.

DSI® system 802 captures a three-dimensional image for each cranial remodeling device. The DSI® image data files 814 comprise DSI® captured three-dimensional image data for each cranial remodeling device. DSI® image data files 814 are arranged as two databases 814R and 814L. The two databases 814R, 814L each correspond to one of two types of cranial remodeling devices, i.e., a right side opening device and a left side-opening device.

Figure 17A:
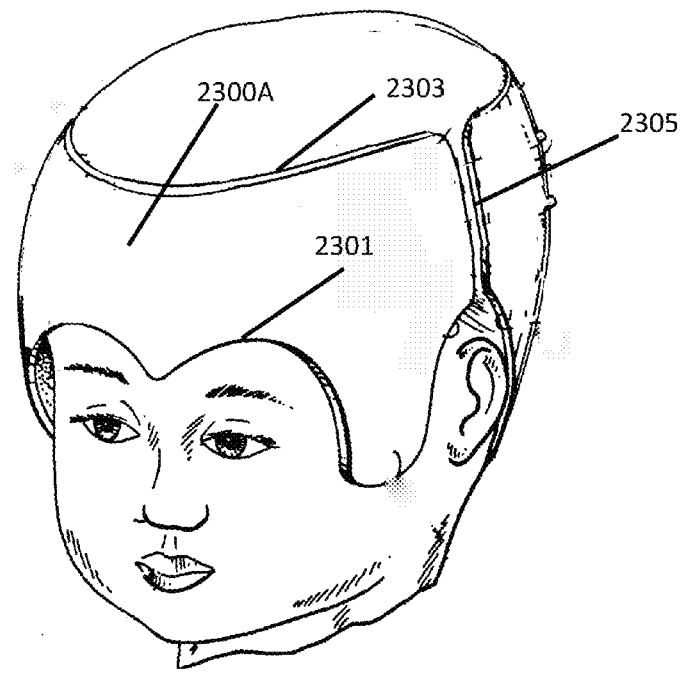
FIGS. 17A and 17B illustrate a cranial remodeling device worn by and off a patient, respectively.
Figure 17B:
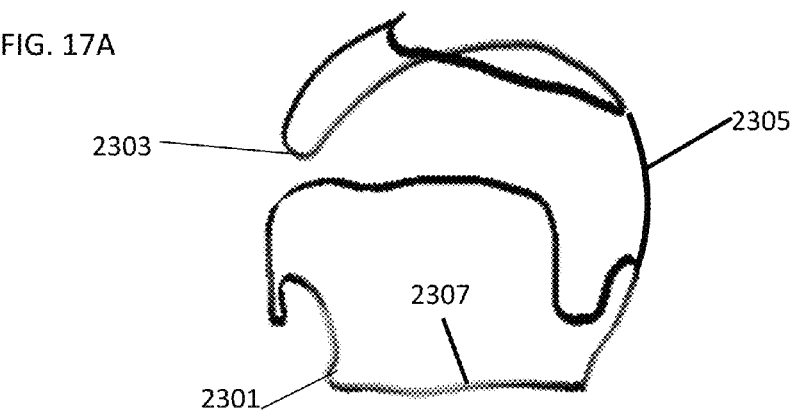

In one embodiment of the invention, the trim lines stored in the two databases 814R, 814L are obtained by capturing and producing a DSI® image data file obtained from prior cranial remodeling devices such as the representative left opening cranial remodeling device 2300A shown in FIG. 17 on an infant and without side closing elements that are typically included on a finished cranial remodeling device 2300A. Trim lines 2301, 2303, 2305 for cranial remodeling device 2300A are shown in FIG. 17B.

Each of the two databases 814R, 814L comprises trim lines 2301, 2303, 2305 for a plurality of its corresponding cranial remodeling device.

Each three-dimensional DSI® image data file of a cranial remodeling device is processed in the same manner as the three-dimensional DSI® image data files for unmodified head shapes are processed as described herein above. The resulting data bases 814R, 814L are each used to separately train a corresponding support vector machine 819R, 819L for generating trim lines for a right side opening device and a left side opening device.

The three-dimensional DSI® cranial mesh for the modified head shape is utilized to provide an input to a three-dimensional milling machine 821. The three-dimensional milling machine 821 manufactures a dimensionally accurate model of the modified head shape from a block of material. It will be appreciated by those skilled in the art that three-dimensional milling machines are commercially available.

One or more layers of copolymer or plastic material are vacuum formed onto the model. In one embodiment a foam layer is first formed onto the model and covered with the one or more layers of copolymer of plastic material. The one or more layers of plastics material, and underlying foam layer, if any, are trimmed or cut to form the cranial modeling device. A detailed description of determining the trim or cut lines is provided below. After the trimming is complete, additional items are added to complete manufacture of the device, such as a fastener arrangement to permit easy putting the cranial device onto and removing it from the subject.

Figure 18:
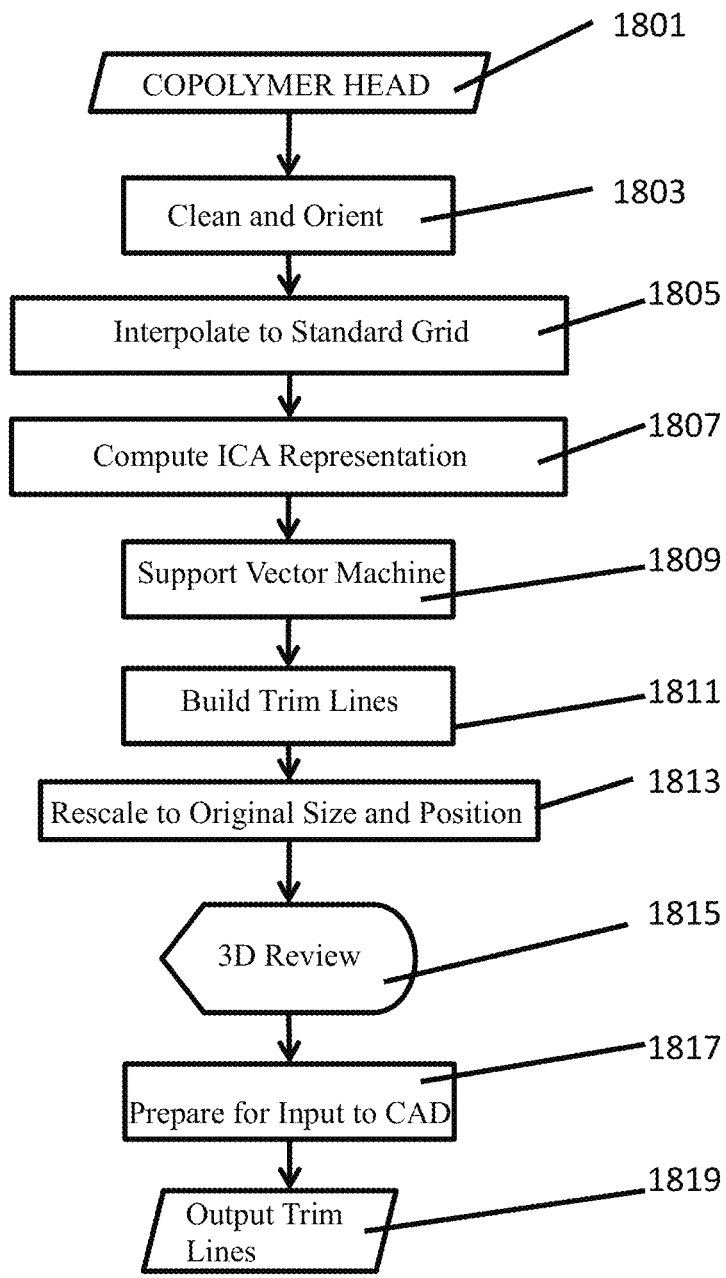
FIG. 18 illustrates methodology steps.

After the plastic material is vacuum formed onto the model, the model with the plastic material formed thereon is scanned utilizing DSI® system 802 to produce a DSI® image data file as shown in FIG. 18 at step 1801.

In the prior DSI® system, it became necessary to cover the model with plastic material formed thereon with a fabric stockinet to obtain accurate quality scans. In the present DSI® system, an algorithm is utilized to account for the specific light absorptive/reflective characteristics of the plastic material such that more detailed, accurate quality scans of the model with plastic material formed thereon can be obtained directly without utilizing a fabric stockinet.

Advantageously, use of the algorithm accounting for the specific absorptive/reflective characteristics of the plastic material utilized to form a cranial remodeling device of the present DSI® system is utilized to directly scan each cranial remodeling device also.

The three-dimensional DSI® image data file of the model with the plastic material formed thereon is cleaned and oriented at step 1803 by eliminating stray polygons, selecting curvature cutoffs, scaling to a Frobenius metric, and orienting to a library reference as described hereinabove.

Alternatively, differential evolution is used to orient the DSI® image data file to a library reference mesh. Differential evolution ("DE") is used to optimize the mutual information in all six degrees of freedom. DE provides optimization by maintaining a population of candidate solutions and creating new candidate solutions by combining existing ones according to its simple formulae, and then keeping whichever candidate solution has the best score or fitness on the optimization.

Following the clean and orient step 1803, the resulting cleaned and oriented three-dimensional DSI® image data file is interpolated to a standard grid at step 1805 by utilizing a bed of nails representation of the model with the plastic material formed thereon.

At step 1807 an ICA representation is computed using ICA program 811 executed on processor 801 to produce a set of 128 ICA coefficients.

One of support vector machines 819R, 819L is utilized at step 1809 to compute a set of trim or cut lines 2301, 2303, 2305. Three sets of trim lines are computed. One set of trim lines 2303 is computed for the top of the cranial remodeling device, one set of trim lines 2301 is computed for the bottom of the cranial remodeling device, and one set 2305 is computed for the sidebar of the device. In one embodiment, support vector machines 819R, 819L compute 129 ICA coefficients for the top trim lines 2303, 129 ICA coefficients for the bottom trim lines 2301, and 3 ICA coefficients for the sidebar trim lines 2305.

Utilizing the ICA coefficients, processor 801 builds the trim lines 2301, 2303, 2305 at step 1811. A set of 256 points is determined for each of the top and bottom trim lines 2303, 2301 and one point is determined for the sidebar.

The resulting trim lines 2301, 2303, 2305 are then rescaled to the original size of the plastic material covered model and re-oriented to the position of the plastic material covered model at step 1813.

Processor 801 may further process the trim lines utilizing a curvature based weighting algorithm to provide smoothed lines. The curvature based weighting algorithm may be in a separate smoothing program.

SVM 817 calculates three IGES curves for each of the three trim lines 2301, 2303, 2305. SVM 817 also calculates a set of three Initial Graphics Exchange Specification (IGES) offset data files. These offset data files permit better definition of the tool orientation when drawing so that the machining or cutting tools always are perpendicular to the surface and don't come in at a glancing angle. The IGES curves for each of the three trim lines 2301, 2303, 2305 are output as three separate colors (RGB). By providing three colors of trim lines, the trim lines are immediately recognizable as to which one was the top, bottom and side trim line.

The Initial Graphics Exchange Specification (IGES) defines a neutral data format that allows the digital exchange of information among Computer-aided design (CAD) systems. The official title of IGES is *Digital Representation for Communication of Product Definition Data*, first published in January, 1980 by the U.S. National Bureau of Standards as NBSIR 80-1978.

A system user can then view the trim lines 2301, 2303, 2305 overlaid onto the three-dimensional digital image of the image data file of the model with the plastic material formed thereon at step 1815. Processor 801 creates a three-dimensional color topographic map of the model. The trim lines are laid on top of the topographic map so that the user can visualize the "terrain" and make sure that the trim lines are in the proper locations.

After the system user selects the desired set of trim lines, the IGES file for the trim lines 2301, 2303, 2305 is prepared as an inputs to a computer aided design/computer aided machine program ("CAD/CAM") at step 1817.

System 1900 further processes the trim lines based upon the varied curvatures over the three-dimensional surface of the shape. Specifically, when a CAD/CAM driven three-dimensional milling machine is utilized, we have determined that it is advantageous to control the machine such that the cut made along the trim lines is always done with the cutting tool perpendicular to the particular surface portion being cut. As the cutting tool progresses along the three-dimensional surface we have determined that it is important to provide an offset to control the angle of the cutting tool such that it is at all times perpendicular to the surface being cut. Accordingly, computer 1801 calculates for each trim line 2301, 2303, 2305 a corresponding offset file to assure that as the cutting tool progresses along the surface, the tool is at all times perpendicular to the surface being cut.

Each commercially available milling machine may have different milling parameters. System 1900 includes an input function such that key milling machine parameters may be entered into system 1900 such that the offset file may be automatically adjusted to customize the offset files for the trim lines to the specific machine utilized. In one embodiment, a spreadsheet function is provided for inputting the offset file and other relevant parameters for the machine being utilized.

The CAD/CAM program is used to operate a three dimensional milling machine 821 carrying a marking tool to first mark the trim or cutting lines onto the vacuum formed plastics material to permit a skilled clinician to verify the correctness of the trim lines.

After the correctness of the trim lines is verified, the marking tool in the milling machine 821 is replaced with a cutting tool and the top, bottom and sidebar cuts are made.

An additional embodiment of the invention is based upon the system and method shown in U.S. Pat. No. 7,227,979 issued Jun. 5, 2007 and U.S. Pat. No. 7,127,101 issued Oct. 24, 2006. The entirety of the disclosures of those patents is incorporated herein by reference. Both of the aforementioned '979 and 101 patents are assigned to the assignee of the present invention.

Figure 19:
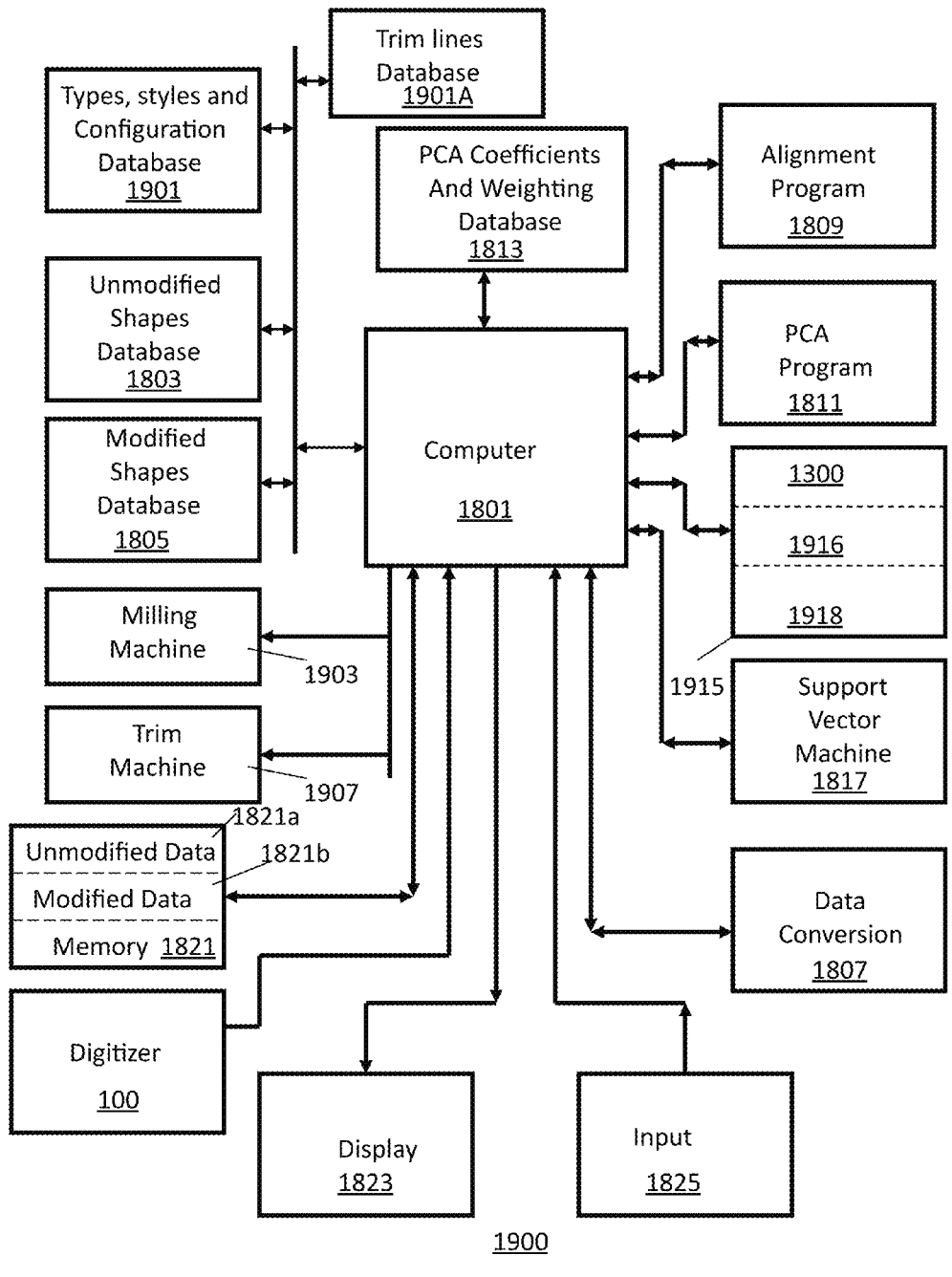
FIG. 19 illustrates a second system.
Figure 20:
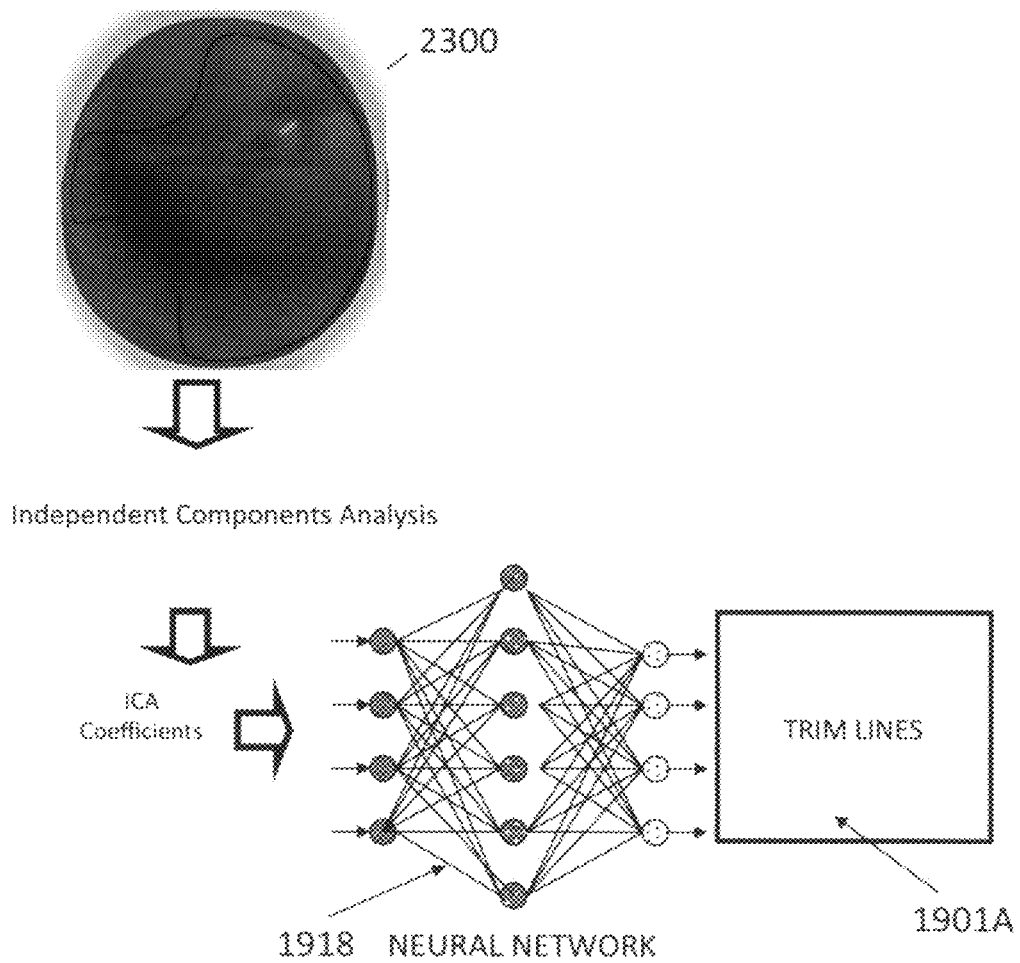
FIG. 20 illustrates the training of a neural network.
Figures 21A, 21B, 21C, 21D, 21E:
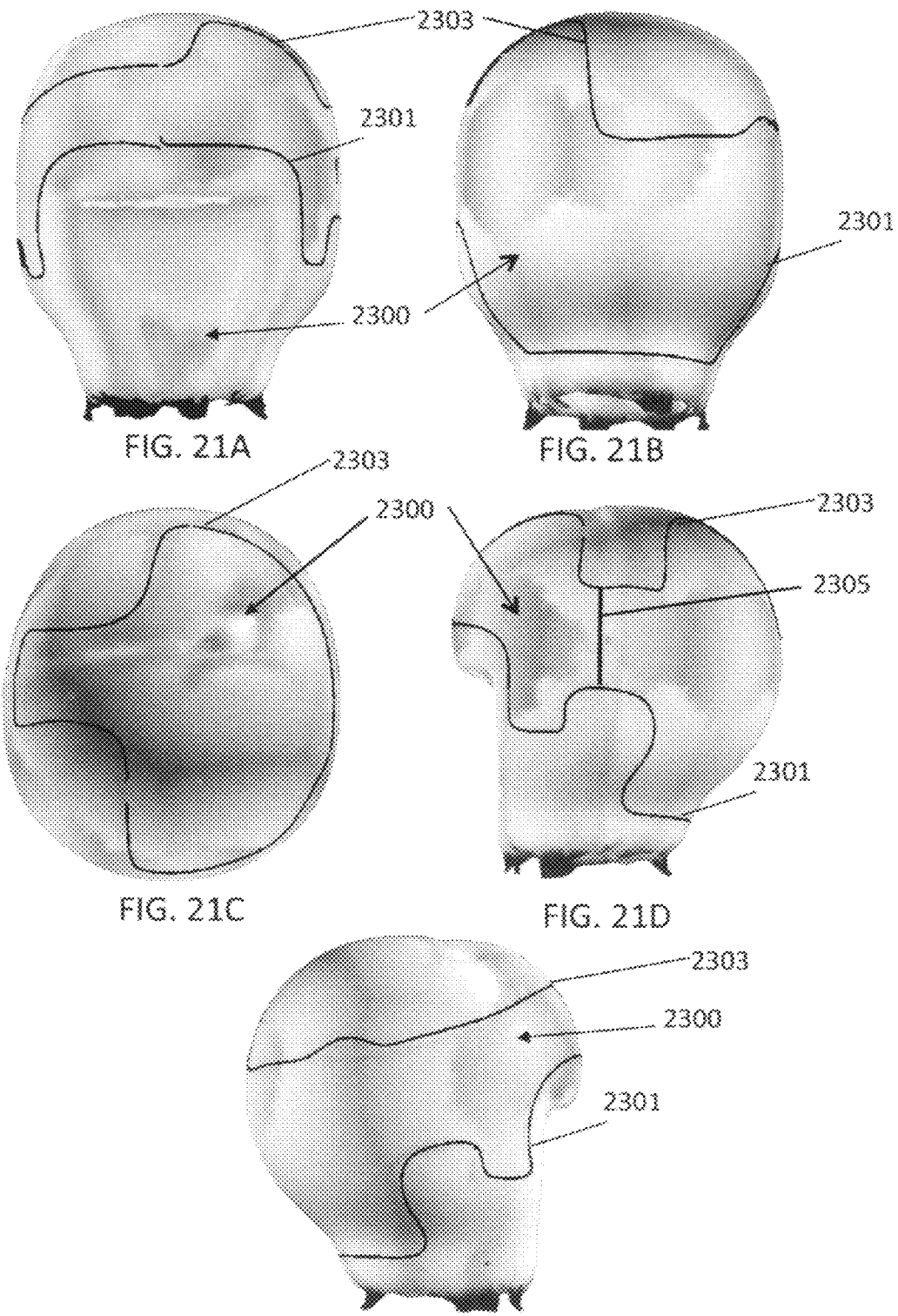
FIGS. 21A, 21B, 21C, 21D, 21E illustrate front, back, top, left and right side views of a model of a modified head shape having copolymer or plastic material thereon and showing cranial remodeling device trim lines marked thereon.

System 1900 shown in FIG. 19 is "trained" as described in the '979 and '101 patents such that it produces a modified head shape for each subject head shape, and the modified head shape is utilized for fabrication of a cranial remodeling device. System 1900 additionally determines a type and style of the cranial remodeling device that is particularly appropriate for the deformity as well as a configuration for the device or band. The type and style of device is determined, in part, from the nature and extent of the cranial deformity and/or from the fit and function of the cranial remodeling band to correct the cranial deformity.

System 1900 comprises a database 1901 that, in turn, comprises for each unmodified head shape dataset data identifying the type and style of cranial remodeling device as well as configuration features.

Neural networks 1915 include a neural network 1300 trained to provide modified shape data from unmodified shape data as described with respect to system 1900. In addition neural networks 1915 includes neural network 1916 that is trained to select a type and style of cranial remodeling device and to select a configuration of the cranial remodeling device.

The methodology for training the neural networks 1916 is described in the '979 and '101 patents. Data for unmodified head shapes obtained from database 1803 and corresponding type, style and configuration data for cranial remodeling devices from database 1901 are utilized to train neural network 1916 such that neural network 1916 will automatically select the type, style and configuration data for a cranial remodeling device.

Neural networks 1915 are trained to generate data representative of a corrected head shape and to select a corresponding cranial remodeling band and features System 1900 includes a milling machine 1903 that receives data from computer 1801 and mills a model. Milling machines are commercially available that will receive digital data from a computer or other digital data source and which produce a milled three-dimensional object.

In system 1900 milling machine 1903 is one such commercially available milling machine. In operation system 1900 instantaneously captures three dimensional image data of an infant's head utilizing digitizer 1819. Computer 1801 stores the captured data 1821a in memory 1821. Computer 1801 then utilizes data conversion module 1807 to convert the data into a "bed of nails" equivalent data and to provide alignment of the captured image and to restore the converted and aligned data in memory 1821. Computer 1801 utilizes neural network 1300 in conjunction with the converted and aligned data of the captured image to produce corresponding three-dimensional DSI® image data for a modified or second head shape. The three-dimensional DSI® data 1821b for the modified or second head shape is stored in memory 1821. In addition, neural network 1916 is also utilized to select a corresponding cranial remodeling band type, style and configuration, which are likewise stored in memory 1821.

Computer 1801 then utilizes the three-dimensional DSI® data 1821*b* for the modified shape to command and direct milling machine 1903 to produce an accurate three dimensional model of the modified shape represented by data 1821*b*.

Computer 1801 also retrieves corresponding cranial remodeling band type, style and configuration features that are displayed on display monitor 1823 to assist in fabricating a cranial remodeling band for the infant whose head was digitally captured.

After milling machine 1903 has produced a three-dimensional representation of a modified head based upon data provided by computer 1801, a copolymer shell is vacuum formed on the representation of the head. The copolymer shell is then shaped to produce the particular device type, style and configuration in a further digital controlled machine 1907.

In addition to data relating to the band type, style and configuration features, a database 1914 is provided. Database 1914 comprises three-dimensional DSI® trim line data for right side opening devices in database 1914R and three-dimensional DSI® trim line data for left side opening devices in database 1914L.

One of neural networks 1918 is trained with trim line data from trim line database 1914R and another of neural networks 1918 is trained with trim line data from database 1914L as illustrated in FIG. 19.

Neural networks 1918 are thus trained to automatically generate trim lines. Once generated, trim line data may be utilized to draw or actually mill trim lines right onto the copolymer or plastic material vacuum formed onto the three dimensional representation of a modified head either utilizing trim machine 1907. Trim machine 1907 may be any one of a number of commercially available machines.

As described above, the data input to the milling machine includes not only trim line data, but offset data that assures that the cutting angle of the cutting tool is at all times perpendicular to the surface of the copolymer or plastic surface.

FIGS. 21A, 21B, 21C, 21D, 21E are front, rear, top, left side and right side of a copolymer covered model with trim lines drawn thereon. Trim line 2301 illustrates the lower margin of cranial remodeling device or band for head shape 2300, trim line 2303 illustrates the upper margin of the cranial remodeling band, and trim line 2305 illustrates the side cut.

In this embodiment, trim lines 2301, 2303, 2305 are hand drawn on the copolymer covered model 2300 of the modified head shape. Data representative of trim lines 2301, 2303, 2305 are captured by using commercially available tracing software and apparatus. The data is then processed and stored in databases 1914R, 1914L and used to train neural networks 1918 as described hereinabove and in the '979 and '101 patents.

Trained neural networks 1918 are then utilized to automatically generate trim lines for use in fabricating cranial remodeling devices.

Advantageously, the various embodiments provide highly accurate manufacture of custom cranial remodeling devices by utilizing an automatically trainable system. The various embodiments provide one or more databases that include three-dimensional data files for head shapes that are captured directly from a plurality of subjects, three-dimensional data files for corresponding modified head shapes; three-dimensional data files for trim lines for corresponding cranial remodeling devices; corresponding data files for trim line offset information; three-dimensional data files for corresponding copolymer or plastic covered models of modified head shapes.

The databases are utilized to train the system such that for each new three-dimensional data file for a head shape, a three-dimensional data file for a modified head shape is automatically generated for producing a cranial remodeling device, and trim lines and corresponding offset lines or data are automatically generated to produce a custom cranial remodeling device.

The databases are automatically updates for each new three-dimensional data file for a head shape that is processed by the system.

The invention has been described in terms of illustrative embodiments. It will be apparent to those skilled in the art that various changes and modifications can be made to the illustrative embodiments without departing from the spirit or scope of the invention. It is intended that the invention include all such changes and modifications. It is also intended that the invention not be limited to the illustrative embodiments shown and described. It is intended that the invention be limited only by the claims appended hereto.

The invention claimed is:

1. A system for producing a custom cranial remodeling device to correct for a cranial shape abnormality of a subject, comprising:

one or more processors;
one or more memories;
a first database comprising a first plurality of first three-dimensional digital data files captured directly from a corresponding plurality of subjects, each said first three-dimensional digital data file captured from an abnormally shaped head;
a second database comprising a second plurality of second three-dimensional digital data files of modified head shapes each corresponding to one of said first database digital data files, each of said second three-dimensional digital data files being generated by said one or more processors operating on a corresponding first three-dimensional digital data files to produce a three-dimensional digital data file of a corrected head shape;
a third database comprising a third plurality of three-dimensional digital data files generated by said one or more processors and each corresponding to three-dimensional trim lines for a corresponding cranial remodeling device of a first type provided for its corresponding second three-dimensional digital data file and either directly captured from said corresponding second cranial remodeling device or generated by said one or more processors;
a fourth database comprising a fourth plurality of three-dimensional digital data files generated by said one or more processors and each corresponding to three-dimensional trim lines for a corresponding cranial remodeling device of a second type provided for its corresponding second three-dimensional digital data file and either directly captured from said corresponding second cranial remodeling device or generated by said one or more processors; and
said one or more processors coupled to said first, second, third, and fourth databases;
said one or more processors operable to receive a captured first three-dimensional digital data file of said subject;
said one or more processors utilizing said captured first three-dimensional digital data file of said subject and said first and second databases to generate a new second three-dimensional digital data file of a modified head shape for said subject;

said one or more processors utilizing said new second three-dimensional digital data file to control apparatus to control manufacture of said custom cranial remodeling device for said patient; and said one or more processors automatically utilizing said captured first three-dimensional digital data file of said subject to select one of said third and fourth databases to generate new trim lines for use in fabricating said custom cranial remodeling device;

said one or more processors automatically processing said new trim lines based upon varied curvatures over the three-dimensional shape of said custom cranial remodeling device to calculate an offset for a cutting tool such that a cut made along said new trim lines by said cutting tool is perpendicular to a surface portion of said custom cranial remodeling device.

2. A system in accordance with claim 1, comprising:

a first program executable by said one or more processors to create trim lines for a cranial remodeling device of said first type, said first program utilizing said third database; and a second program executable by said one or more processors to create trim lines for a cranial remodeling device of said second type, said second program utilizing said fourth database; and said one or more processors operable to determine whether said custom cranial remodeling device is of said first type or said second type to select said first program or said second program to generate said new trim lines and to execute said selected first program or said second program.

3. A system in accordance with claim 2, comprising:

first apparatus operable response to said one or more processors to generate a three dimensional model of a desired head shape;

second apparatus operable to form plastic material onto said three-dimensional model; and said one or more processors selectively utilizing one of said first program and said second program to generate said trim lines for said plastic material formed onto said model and to calculate said offset to produce said custom cranial remodeling device.

4. A system in accordance with claim 3, comprising:

said one or more processors generate a plurality of sets of trim lines for said plastic material formed onto said model.

5. A system in accordance with claim 4, comprising:

an operator viewable display;

said one or more processors generate a three-dimensional image on said display of said plastic material formed on said model; and said one or more processors overlay one set of a plurality of sets of trim lines onto said three-dimensional image.

6. A system in accordance with claim 5, wherein:

each said set of trim lines of said set of trim lines is displayed in a different color.

7. A system in accordance with claim 4, wherein:

said one or more processors generate a three-dimensional color topographic image on said display of said plastic material formed on said model.

8. A system in accordance with claim 7, wherein:

said one or more processors overlay one set of trim lines onto said three-dimensional color topographic image.

9. A system in accordance with claim 2, comprising:

first apparatus operable to generate a three dimensional model of a corrected head shape for said subject;

second apparatus operable to form said plastic material onto said model;

said one or more processors selectively executing one of said first and said second programs to generate trim lines for said plastic material formed onto said device; and said one or more processors generate offset data corresponding to each of said trim lines, said offset data utilized such that a tool cutting said plastic material cuts perpendicular to the surface of said plastic material.

10. A system in accordance with claim 9, comprising:

said one or more processors provides a spreadsheet function to input parameters for a milling machine carrying said cutting tool; and said one or more processors generates said offset data in accordance with said input parameters.

11. A system in accordance with claim 2, comprising:

said one or more processors updates and adds to each of said first database and said second database, and one of said third database or said fourth database with each new custom cranial remodeling device.

12. A system: in accordance with claim 1, comprising:

a first apparatus for directly capturing a three-dimensional digital data image file of said subject;

said one or more processors is operable to manufacture a model of said corrected a head shape for said subject;

apparatus for forming one or more layers onto said model, the outer one of said layer comprising a copolymer;

apparatus for directly capturing a three-dimensional digital data image file of said model having said copolymer layer; and said one or more processors operable to generate trim lines for said cranial remodeling device utilizing said three-dimensional digital data image file of said model.

* * * * *